(12) United States Patent
MacLullich et al.

(10) Patent No.: US 9,307,940 B2
(45) Date of Patent: Apr. 12, 2016

(54) APPARATUS AND METHOD FOR TESTING SUSTAINED ATTENTION AND DELIRIUM

(75) Inventors: Alasdair MacLullich, Edinburgh (GB); Laura Brown, St. Andrews (GB); Jonathan Adler, Edinburgh (GB)

(73) Assignee: THE UNIVERSITY COURT OF THE UNIVERSITY OF EDINBURGH, Edinburgh (GB)

(*) Notice: Subject to any disclaimer, the term of this patent is extended or adjusted under 35 U.S.C. 154(b) by 451 days.

(21) Appl. No.: 13/500,371

(22) PCT Filed: Oct. 7, 2010

(86) PCT No.: PCT/GB2010/001885
§ 371 (c)(1),
(2), (4) Date: Jun. 29, 2012

(87) PCT Pub. No.: WO2011/042703
PCT Pub. Date: Apr. 14, 2011

(65) Prior Publication Data
US 2012/0271194 A1    Oct. 25, 2012

(30) Foreign Application Priority Data
Oct. 7, 2009   (GB) .................................. 0917600.9

(51) Int. Cl.
*A61B 13/00* (2006.01)
*A61B 5/16* (2006.01)
*A61B 5/00* (2006.01)
(Continued)

(52) U.S. Cl.
CPC ................. *A61B 5/16* (2013.01); *A61B 5/4088* (2013.01); *A61B 3/02* (2013.01); *A61B 3/113* (2013.01); *A61B 5/162* (2013.01); *A61B 5/165* (2013.01); *A61B 5/168* (2013.01)

(58) Field of Classification Search
CPC .......... A61B 5/16; A61B 5/162; A61B 5/165; A61B 5/168; A61B 3/02; A61B 3/113
USPC ........................................................ 600/558
See application file for complete search history.

(56) References Cited

U.S. PATENT DOCUMENTS

| 4,770,636 A | * | 9/1988 | Buschke ................. 434/236 |
| 5,801,810 A | * | 9/1998 | Roenker ................. 351/246 |
| 6,364,486 B1 | * | 4/2002 | Ball et al. ................. 351/203 |

(Continued)

FOREIGN PATENT DOCUMENTS

WO    03075762    9/2003

OTHER PUBLICATIONS

Dormal et al. "Dissociation of numerosity and duration processing in the left intraparietal sulcus: A transcranial magnetic stimulation study", Cortex, vol. 44, Issue 4, Apr. 2008, pp. 462-469.*

(Continued)

*Primary Examiner* — Devin Henson
(74) *Attorney, Agent, or Firm* — Snell & Wilmer L.L.P.

(57) ABSTRACT

A testing apparatus for testing a user's sustained attention comprises at least one stimulus-provider and a controller for controlling the stimulus-provider to provide at least one target stimulus, wherein the controller is configured to perform at least one operating procedure and the or each operating procedure comprises controlling the stimulus-provider to provide a sequence of target stimuli to the user.

14 Claims, 14 Drawing Sheets

(51) Int. Cl.
A61B 3/113 (2006.01)
A61B 3/02 (2006.01)

(56) References Cited

U.S. PATENT DOCUMENTS

| | | | |
|---|---|---|---|
| 7,163,513 B2* | 1/2007 | Darby et al. | 600/558 |
| 2005/0110950 A1* | 5/2005 | Thorpe et al. | 351/209 |
| 2009/0281398 A1* | 11/2009 | Hogan | 600/301 |

OTHER PUBLICATIONS

European Patent Application 10771500.5 Examination Report dated Apr. 7, 2014.
"Attentional deficits in derlirium: a systemic investigation" Zaghdani et al.: Psychology Undergraduate Thesis Collection [Online], Jul. 1, 2009, pp. 1-102 and 1-109.
"Cognitive visual perceptual deficits in patients with delirium", Laura J.E. Brown, et al., Journal of Neurology Neurosurgery & Psychiatry, Jul. 1, 2009, pp. 594-599.
International Search Report for PCT/GB2010/001885 dated Dec. 22, 2010.
International Preliminary Report on Patentability dated Apr. 11, 2012 in Application No. PCT/GB2010/001885.
Hart et al, 'Abbreviated Cognitive Test for Delirium', Journal of Psychosomatic Research, vol. 43 No. 4 pp. 417-423 (1997).
Hart et al 'Validation of a Cognitive Test for Delirium in Medical ICU Patients', Psychosomatics, vol. 37, No. 6, p. 533-546 (1996).
Lowery et al 'Quantifying the association between computerised measures of attention and confusion assessment method defined delirium: a prospective study of older orthopaedic surgical patients, free of dementia', International Journal of Geriatric Psychiatry, pp. 1-8 (2008).
Inouye et al 'Clarifying confusion: the Confusion Assessment Method. A new method for detection of delirium' Annals Internal Medicine, 113: pp. 941-948 (1990).
Simon et al 'Reliability of a structured assessment for nonclinicians to detect delirium among new admissions to postacute care' Journal of American Medical Directors Association, 77: pp. 412-415 (2006).
ICD-10: The ICD-10 Classification of Mental and Behavioural Disorders: Clinical Descriptions and Diagnostic Guidelines, 1992, World Health Organisation pp. 47-51 Dementia in Alzheimer's disease; Vascular dementia.
Breitbart et al, 'The memorial delirium assessment scale', Journal of Pain and Symptom Management, vol. 13 Issue 3 p. 128-137 Mar. 1997.
Meagher et al, 'Defining delirium for the International Classification of Diseases, 11th Revision', Journal of Psychosomatic Research, 65 (2008) pp. 207-214.
Laurila et al, 'Delirium among patients with and without dementia: does the diagnosis according to the DSM-IV differ from the previous classifications?' International Journal of Geriatric Psychiatry, vol. 19 Issue 3 p. 271-277 (2004).
Mendez MF, Cherrier MM and Perryman KM, "Differences between Alzheimer's disease and vascular dementia on information processing measures". Brain and Cognition, 1997, 34, 301-310.
Brown LJ, Fordyce C, Zaghdani H, Starr JM, MacLullich AM. "Detecting deficits of sustained visual attention in delirium". J Neurol Neurosurg Psychiatry. 2011;82:1334-40.
Tsal Y, Shalev L, Mevorach C. The diversity of attention deficits in ADHD: the prevalence of four cognitive factors in ADHD versus controls. J Learn Disabil. 2005;38(2):142-57.

* cited by examiner

Button Responses

APPARATUS AND METHOD FOR TESTING SUSTAINED ATTENTION AND DELIRIUM

CROSS-REFERENCE TO RELATED APPLICATIONS

This application is a U.S. national phase filing under 35 U.S.C. §371 of PCT/GB2010/001885 filed Oct. 7, 2010, the entire contents of which is incorporated herein by reference.

FIELD OF THE INVENTION

The present invention relates to testing apparatus and methods, for example testing apparatus and methods for determining a user's ability to sustain attention. The apparatus and methods may be used as part of a determination of the presence or absence of delirium.

BACKGROUND TO THE INVENTION

Delirium (or 'acute confusional state') is a severe neuropsychiatric disorder characterised by acute and fluctuating deficits in attention, arousal and cognitive function. Despite the prognostic importance of early diagnosis and treatment of delirium, it is currently under-studied and is under-detected in clinical settings.

'Inattention' is recognised as being one of the core features of delirium. However, the particular aspects of attentional disturbance associated with this feature have not been well characterised. Rather, these attentional deficits have more typically been described in patients using subjective clinical expressions, such as 'being easily distractible' or 'having difficulty paying attention'. This is important because a better understanding of the specific neuropsychological processes that are impaired in delirium may provide key insights to understanding the pathophysiological mechanisms that underlie it. Clinical tests that can reliably detect attentional deficits may be particularly useful for providing diagnostic measures that are sensitive to delirium. However, there is overlap between the neuropsychological features of delirium and those of other conditions, for example dementia, and many known tests that can detect attentional deficits cannot distinguish reliably between delirium and such other conditions. This may be because (a) the tests are too challenging, such that even the milder attentional deficits observed in mild to moderate Alzheimer's dementia are enough to result in reduced scores, and (b) because the category or type of attentional deficits are not specific to delirium.

The Cognitive Test for Delirium (CTD), as described by Hart et. al. in "Abreviated Cognitive Test for Delirium", Journal of Psychosomatic Research, Vol. 43, No. 4, pages 417-423 (1997) and also in "Validation of a Cognitive Test for Delirium in Medical ICU Patients" in Psychosomatics, Volume 37, Number 6, page 533 (1996), includes two tasks that require patients to listen to strings of serially-presented letters, and to make a response each time a given target letter is heard. These tasks therefore depend on the ability to sustain attention to auditory information over an extended period of time. Intensive care patients with delirium show impairments on these tasks, indicating the presence of sustained attentional deficits, and the test may be able to provide some distinction between patients with delirium and patients with depression, dementia or schizophrenia. However, the tests have a significant subjective element as they are performed by a human tester, and the outcome of the tests may depend on the way in which the tests are performed by the tester. Moreover, given the auditory nature of these tasks, it is unclear how well these tasks would transfer into noisier, general ward settings. In addition, the patient's performance on the task does not tell us whether they also have deficits in attending to information from non-auditory modalities, such as vision or touch.

Lowery et al, in "Quantifying the association between computerised measures of attention and confusion assessment method defined delirium: a prospective study of older orthopaedic surgical patients, free of dementia", Int J Geriatr Psychiatry (2008), DOI: 10.1002/gps.2059, showed that patients with delirium also perform worse than cognitively-healthy control patients on two computerised tasks that involve sustained attention to visual information. In these tasks, patients were required to attend to series of visual stimuli, and to make speeded button responses to particular target stimuli. The information was presented on a high resolution computer screen, and the responses recorded via a module containing two buttons, one marked 'NO' and the other 'YES'. The test took approximately 5 minutes to perform, and included the Digit Vigilance (DV) and Choice Reaction Time (CRT) tasks. For the DV task, the participants were required to use the module to identify multiple presentations of a 'target' digit within a two minute period of serially presented 'target' and 'distracter' digits. The CRT task required the participant via the module to press either 'NO' or 'YES' as they appeared on the screen. Twenty presentations of either stimulus were displayed sequentially with a varying inter-stimulus interval. The DV task provided a measure of ability to sustain attention through accuracy of response. The CRT task provided two measures, Mean reaction time (msec) and intra-trial variability of reaction time (standard deviation of the reaction times across 90 sec for each individual participant).

However, as these tasks require relatively rapid perceptual processing of visual information, and also the speeded formulation and execution of motor responses, they are not specific to detecting attentional deficits, that is, they depend on adequate functioning of several cognitive domains other than sustained attention, indeed, patients with Alzheimer's dementia are known to perform poorly on these tasks, thereby limiting their specificity to detecting delirium. Furthermore, as patients with delirium have also been shown to have deficits in visual perceptual processing, it is possible that some of their difficulties on these tasks may in fact reflect the perceptual demands of the tasks rather than the attentional components.

SUMMARY OF INVENTION

According to a first aspect of the present invention, there is provided a testing apparatus for testing a user's sustained attention, comprising at least one stimulus-providing means (for example a stimulus-providing device) and a controller for controlling the stimulus providing means to provide at least one target stimulus, wherein the controller is configured to perform at least one operating procedure and the or each operating procedure comprises controlling the stimulus-providing means to provide a sequence of target stimuli to the user.

By providing such an apparatus, automated testing for conditions such as delirium, that affect sustained attention may be obtained. As other conditions such as dementia affect attention in a different way, such testing may distinguish between delirium and such other conditions. Furthermore, by providing an apparatus that is operable to provide at least one stimuli, the testing for sustained attention can be made objective, removing or reducing the influence of the behaviour of a human tester during performance of the test.

The at least one target stimulus may have at least one property that enables a measure of a user's sustained attention to be determined from a response or responses of the user to the at least one target stimulus. The at least one property may comprise the timing, duration, intensity or other property of the or each stimulus or, for a plurality of stimuli, the separation in time of the stimuli, and/or variations in properties of different ones of the stimuli.

The stimulus providing means may comprise a light source or display, which may comprise a bulb, a LED, a LCD, an OLED or the like. The stimulus providing means may comprise a tactile stimulus providing means, that may comprise a vibration unit. The stimulus providing means may comprise an audible stimulus providing means, which may be operable to provide stimuli in the form of sounds such as buzzes, beeps or tones. The audible stimulus providing means may be arranged to provide audible stimuli via headphones.

The target stimuli may comprise visual and/or tactile and/or audible stimuli. The use of visual and/or tactile stimuli may be particularly useful in clinical or other environments where there may be significant background noise and where users may be better able to process visual/tactile stimuli than audible stimuli.

The apparatus may comprise two or more stimulus providing means.

It has been found that the number of target stimuli included in a sequence of an operating procedure, and/or the duration of each target stimulus, and/or the duration of the operating procedure, and/or the separation in time between target stimuli in the sequence, and/or or other properties of stimuli or sequences of stimuli can have a significant impact on the effectiveness of user responses to the stimuli presented during the operating procedure in determining the presence of delirium, and in distinguishing delirium over other conditions.

In order to provide an apparatus that can be used to detect the presence of delirium and that can distinguish delirium from other conditions, for example dementia, it can be important for the apparatus to provide a test that requires effortful sustaining of attention, retention of task instructions, and absence of a requirement for cognitive processing that is too difficult. The control of inter-stimulus delays in particular to have appropriate values has been found pursuant to the present invention to be important in placing a level of demand on the user that is appropriate for the detection of delirium. For example if the inter-stimulus delays are too long then the user may lose attention too easily to provide an accurate test, whereas if the delays are too short the cognitive demands placed on the user may be too great. Delays of between 800 ms and 4500 ms, in particular between 2050 ms and 4050 ms, between stimuli have been found to be particularly useful in detecting delirium and distinguishing it from other conditions.

By providing for such a delay, the testing may be more sensitive to delirium, and/or more able to distinguish delirium from other conditions. Such a relatively slow pace of testing may be important, as it may place greater demands on the capacity for sustained attention. It has been suggested that the optimal speed of presentation of stimuli for ease of counting up may be about one stimulus per second. By extending the gaps between stimuli to be greater than 1 second, and particularly 3 seconds or more, the kind of attentional deficits that are particularly important in delirium may be more effectively elicited.

The apparatus may be adapted to provide a delay between target stimuli. The delay between stimuli may be variable and/or random. The delay may be greater than 1000 ms. The delay may be between 800 ms and 4500 ms, optionally between 2050 and 4050 ms.

The delay may be substantially equal to or greater than 3000 ms

Each operating procedure may comprise presentation of a sequence of between 1 and 30 stimuli, optionally between 5 and 14 stimuli. That number of stimuli has been found to be particularly useful in determining the presence of delirium. For example, if fewer stimuli are provided, then a patient with delirium may have less difficulty in maintaining attention for the duration of the operating procedure, which may make the test less sensitive to delirium, whereas if more stimuli are provided patients with delirium and with other conditions may have increasing difficulty in maintaining attention for any of the additional stimuli in the sequence, and later stimuli in the sequence may become increasingly less useful in distinguishing between delirium and other conditions. Operating procedures comprising between 1 and 4 stimuli may be provided, which may be usable in determining if a patient is capable of following the task instructions. Operating procedures comprising between 15 and 30 stimuli may be provided, which may be usable to allow for testing of more subtle inattention.

The apparatus may be arranged to display the stimulus for a duration in the range 200 ms to 2000 ms, preferably between 600 ms to 1400 ms. The duration may be substantially equal to 1000 ms. By displaying each target stimulus for such durations, the effects of any deficit in the visual processing or reaction time of the user may be reduced, and the testing may be more selective for determining sustained attention deficit.

Each operating procedure may be arranged to last for a duration of between 7 seconds and 180 seconds.

As mentioned above, the duration of the stimulus and the delays and the overall duration of the operating procedure may be important as correct selection of the stimulus, delay durations and number of stimuli may increase the selectivity of the test in determining ability to sustain attention and minimise other influences such as slow processing of information, slow reaction times and slow formulation and executing of responses.

The apparatus may further comprise monitoring means for monitoring a response from a user to the or each target stimulus. The monitoring means may be included in or configured to co-operate with the controller.

The monitoring means may be configured to monitor input received from a user via the or each input device. The at least one input device may comprise a plurality of input devices, and for each target stimulus the monitoring means may be configured to monitor for a response from a respective selected one of the input devices.

The monitoring means may be adapted to determine a reaction time and/or average reaction time, which may be storable in a memory. The reaction times may be usable in conjunction with cueing means in order to determine the effects of endogenous attention shifts, as a user who has moved their attention to a stimulus providing means before the target stimulus is provided may be expected to give a faster response to the target stimulus.

A user may provide a response, for example a single response, after an operating procedure. The single response may comprise a user assessment of the number of times a stimulus has been provided by the apparatus during the procedure. Thus, a counting test may be provided. The response may be provided to (for example spoken to) an operator, and a data input means may be provided for the operator to enter the response. Alternatively, the user input means may comprise means for entering the response.

The apparatus may be adapted to provide a response time frame for responding to a stimulus, wherein a response to a target stimulus is treated as valid if it is made within the response time frame. The monitoring means may be configured to monitor for a response to a stimulus within or otherwise in dependence on the response time frame. The response time frame for responding to a stimulus may begin a lag time after the stimulus is initiated. The response time frame for responding to a stimulus may end a further lag time after the stimulus is no longer provided. The lag time may be within the range 50 ms to 200 ms, and/or 100 ms to 150 ms. The further lag time may be within the range 50 ms to 1000 ms, and/or 100 ms to 500 ms. The time frame for responding to a stimulus may lie between 100 ms and 2000 ms from the start of the stimulus. The time frame may have a duration of between 500 ms and 2000 ms, and/or between 1000 ms and 1500 ms.

By providing a time frame for responding that only starts after provision of the stimulus has begun, a margin to account for response time is left between the stimulus being provided and the window for responding. In this way, pre-emptive speculative response inputs may be disregarded and the accuracy of the system increased. By allowing input responses to be made for a period after the target stimulus has been removed, the effect of slow reactions, processing or responses of the user is minimised.

It has been found to be important to provide the appropriate response time frame for a user response to a stimulus to be treated as valid in order to provide suitable demands on the user to enable selective detection of delirium. If the response time frame is too long then random or speculative responses by a user not linked to a stimulus may incorrectly be classified as valid responses. If the response time frame is too short then the cognitive and/or motor response demands placed on the user may be too great.

The apparatus may comprise or be provided within a housing. The housing may be a sealed or sealable housing. By providing the device in a sealed or sealable housing, it may be easily cleanable with alcohol gel and other disinfectants and/or more resistant to harbouring or transmitting infection, which may be particularly important in a clinical environment.

The apparatus may be operable as a portable and/or stand-alone device. In this way, the apparatus may be easily portable, for example, to a patient's bedside or on top of an overbed table, which is especially convenient, particularly for infirm patients.

The stimuli producing means and/or the or a distraction producing means may be arranged to be hidden when not illuminated. The stimuli producing means and/or the distraction producing means may be located behind an opalescent member.

The apparatus may comprise a substantially plain surface, and the stimuli producing means may be provided on the substantially plain surface. Thus, any extraneous distractions may be reduced. The substantially plain surface may exclude substantially all user input devices or stimulus providing means other than those used for testing attention or recording a user's response. The substantially plain surface may be a substantially plain surface of the housing. The substantially plain surface may be a metal or plastic surface. The housing may exclude a keyboard.

It has been found to be important to control the level of distraction and the cognitive demands placed on the user in order to provide for successful detection for the presence of delirium. The provision of the apparatus in a housing having a substantially plain surface can provide for a device that is easily useable and that does not provide excessive inherent cognitive demands on a user. In contrast a test implemented using a PC or other personal computer, or computer terminal with a keyboard, can be inherently confusing or distracting for users that are suffering from delirium or other conditions, and such confusion or distraction can interfere with successful testing.

The apparatus may be adapted to receive and/or to be fixable to a transparent and flexible cover, which may be single-use and disposable, or washable. The cover may be a plastic cover. The cover may allow a patient to observe the stimuli, and also to press the response buttons.

The stimulus providing means may comprise at least one light provided on the surface of the housing, optionally one or two lights provided on the surface of the housing.

The or each light may comprise a lightable button and the or each lightable button may be configured to operate as a user input device.

The use of lightable buttons as both stimulus and user input device has been found to be particularly suitable in testing for the presence of delirium, as the cognitive and physical demands of viewing and operating the buttons is not excessively demanding for users who may be suffering from delirium and other conditions, so that operation of the buttons does not place unwanted additional demands on the user.

The apparatus may comprise one or more distraction providing means (for example, one or more distractors) for providing distraction stimuli. The distraction providing means may be separate from the stimulus providing means. The distraction providing means may be adapted to be distinctive from the stimulus providing means. For example, the distraction providing means and/or the distraction stimuli produced thereby may be a different colour, size, shape, location, light source type, appearance, brightness, texture, feel (such as degree of vibration), duration and/or temperature to the target stimuli and/or stimulus providing means. One or more distraction providing means may be adapted to produce distraction stimuli in a different modality to at least one stimulus providing means and/or at least one other distraction providing means. The distraction providing means may be arranged to provide visual and/or tactile and/or audible distraction stimuli.

The distraction providing means may comprise a light source or display, which may comprise a bulb, a LED, a LCD, an OLED or the like. The distraction providing means may comprise a tactile stimuli providing means, which may comprise a vibration unit. The distraction providing means may comprise an audible stimulus providing means, which may be operable to provide stimuli in the form of sounds such as buzzes, beeps or tones. The audible stimulus providing means may be arranged to provide audible stimuli via headphones.

The distraction providing means can be used to provide another control over the level of demand placed on the user. The provision of separate distraction providing means has been found to be particularly useful as it can enable separate control of distraction without interfering with the timings of the sequence of stimuli of an operating procedure.

The apparatus may comprise means for directing a user's attention to a predetermined location, for example a fixation point. The means for directing a user's attention may comprise the fixation point, which may be an illuminable fixation point. The fixation point may be centrally mounted on the device, for example centrally mounted between two or more stimulus providing means. The illuminable fixation point may be provided with an opalescent cover, which may be adapted so that the illuminable fixation point is hidden when unlit but becomes visible when lit. The fixation point may be in the form of a cross. By providing the fixation point, the device encourages the user to look at the centre of the box before each trial begins.

The apparatus may comprise at least one and optionally a plurality of input devices. The at least one input device may be for receiving input from a user in response to the at least one target stimulus. The apparatus may comprise a communications module for communicating with a user. The at least one input device may form part of the communications module. Each input device may be adapted to receive tactile and/or motor responses to the stimuli. The input device may comprise at least one button. The tactile and/or motor response may comprise pushing the button. The or each input device may provide tactile feedback, for example vibro-tactile feedback, or other feedback to a user in response to input from the user via the input device. For example, a button may vibrate if pressed.

The apparatus may comprise cueing means. The cueing means may be arranged to alert a user that a stimulus will be provided, which may be before the stimulus is actually provided. The cueing means may be located at or adjacent the stimulus providing means. The cueing means may be located at or adjacent the fixation point. The cueing means may comprise visual and/or tactile and/or audible alerts. The cueing means may comprise a light source, which may comprise an LED. The fixation point may also be operable as the cueing means.

The cueing means may be distinctive from the stimulus providing means. For example, the cueing means and/or the alerts produced thereby may be a different colour, size, shape, location, light source type, appearance, brightness, texture, feel (such as vibrating or not), duration and/or temperature to the target stimuli and/or stimulus providing means.

The apparatus may comprise a plurality of cueing means, which may include associated cueing means associated with a stimulus providing means and/or at least one neutral cueing means that is not associated with any particular stimulus providing means. The neutral cueing means may be separated from the stimulus proving means. The associated cueing means may be located adjacent the stimulus providing means with which it is associated. The cueing means may be located at corners of its associated stimulus providing means.

The cueing means may be provided in the form of an indicator, such as an arrow. The associated cueing means may be arranged to provide an indication of an associated stimulus providing means.

By providing a cue or alert to warn the user of an imminent target stimulus an/or which stimulus providing means will provide the target stimulus, the effects of endogenous attention shifts (i.e. when a user voluntarily shifts their attention to a particular area because they expect a target stimulus to be provided there) can be determined.

The or at least one of the stimulus providing means may be integral with the or at least one of the input devices. The monitoring means may be configured to monitor the response via an input device to a stimulus provided by a stimulus providing means which that input device is integrated and/or associated.

The communications module may be adapted to communicate with a computer. The apparatus may be programmable via a computer.

The apparatus may be provided with a processor and memory. The apparatus may comprise a battery for powering the device. The processor may comprise at least part of the controller.

The controller may be configured to control the stimulus providing means to control the timing and/or duration of the or each target stimulus. The controller may be configured to perform one or more operating procedures. The controller may be configured to perform each operating procedure separately.

An operating procedure may comprise a sequence of one or more stimuli and/or delays and/or distractions. The controller may be configured to process sequence data representative of the number of target stimuli in a sequence and/or the duration of each stimuli, and/or the duration of the sequence, or to process sequence algorithm data for generating such sequence data, and to control the stimulus providing means to perform an operating procedure comprising the sequence. The sequence data and/or the sequence algorithm data may be stored in the memory.

The or each operating procedure may be selectable from a plurality of operating procedures. The stimuli and/or delays and/or distractions of each operating procedure may be programmable.

The apparatus may be adapted to perform a test comprising a plurality of operating procedures. Each operating procedure in a test may differ from at least one other operating procedure in the test. Each operating procedure may differ in the method of user response or input. Each operating procedure may differ in the distraction provided, for example in whether or not distraction is provided or the amount of distraction provided. Each operating procedure may differ in the number of stimuli producing means used. Each operating procedure may differ in the type of stimuli used.

The apparatus may be adapted to provide selection and/or creation and/or editing of operating procedures and/or tests via the computer and/or input device. The memory may be arranged to store the operating procedures and/or tests. The processor may be arranged to implement the operating procedures and/or tests.

The apparatus may be arranged to provide at least first and second stimuli. The first and second stimuli may be provided by different stimulus providing means. The monitoring means may be configured to monitor responses of a user to one or both first and second stimuli.

The apparatus may be adapted to operate the distraction providing means to provide the distraction stimuli during provision of target stimuli. The apparatus may be adapted to provide the distraction stimuli between provision of target stimuli. The apparatus may be adapted to provide the distraction stimuli both during and between target stimuli.

Each distraction stimulus may be provided for a shorter time than the target stimuli. Each distraction may be displayed for 200 ms or less.

Performance of the test may be improved if the distraction stimuli are distinctive from the target stimuli, as this may minimise effects due to slow processing of deformation and increases the selectivity of the apparatus. By having distraction stimuli that are distinctive from the target stimuli, confusion between the target stimuli and the distraction stimuli may be minimised, thereby making the apparatus more selective for attentional deficits rather than deficits in perception and/or comprehension.

The apparatus may be an apparatus for determining sustained attentional performance.

Processing means for processing the responses of a user to the target stimuli to determine a measure of sustained attention for a user may be provided. The processing means may be included in or configured to communicate with the apparatus. The processing means may be configured to determine a respective measure of sustained attention from the responses obtained for each operating procedure. The measure of sustained attention may also be referred to as a measure of sustained inattention.

The processing means may be configured to combine the determined measure of sustained attention for each operating procedure of a test to obtain a combined measure of sustained attention for the test. Alternatively, or additionally the processing means may be configured to process the responses obtained for each operating procedure together to obtain the measure of sustained attention.

The processing means may be configured to determine the measure of sustained attention in dependence on at least one of the presence or absence of a response to at least one stimulus; the correctness of the response to at least one stimulus; the timing of the response (for example delay in responding to) to the at least one stimulus; the variation during the duration of a test in the presence or absence of response and/or the correctness of response and or the timing of response.

The memory may be adapted to store a look-up table. The look-up table may be arranged to store correlation data for correlating the number of valid responses with a measure of attention. The processing means may be adapted to determine the or a measure of sustained attention of the user by comparing the number of valid responses with the correlation data.

The processing means may be configured to compare the determined measure to a threshold and to provide an output in dependence on whether the determined measure is greater than the threshold.

The apparatus may be an apparatus for determining delirium.

The apparatus may be further adapted to use the measure of sustained attention/inattention of the user to determine a level of delirium in the user. The apparatus may be arranged to compare the measure of sustained attention with a threshold value and return an indication of whether or not a user may suffer from delirium dependent on whether the measure of sustained attention is above or below the threshold.

In another independent aspect of the invention there is provided a testing apparatus, the apparatus comprising at least one stimulus-providing means and a controller for controlling the stimulus providing means to provide at least one target stimulus, for example such that a user's sustained attention to the at least one target stimulus can be determined.

According to a further aspect of the invention is a method of determining sustained attentional performance, the method comprising providing at least one target stimulus and determining a user's sustained attention to the at least one target stimulus.

The method may comprise providing an apparatus comprising at least one stimulus providing means and operating the at least one stimulus providing means to provide the at least one target stimulus. The apparatus may comprise an apparatus according to the first aspect.

The method may comprise providing a plurality of stimuli.

The method may comprise determining a response of a user to the or each target stimulus, and determining a measure of the user's sustained attention in dependence on the response to the or each target stimulus. The method may comprise monitoring the response of the user to the or each target stimulus. The monitoring may comprise monitoring for the presence or absence of a response, for example a correct response, and/or monitoring the time between the provision of a target stimulus and receipt of a response.

The target stimuli may comprise visual and/or tactile and/or audible stimuli.

The method may comprise providing distraction stimuli. The distraction stimuli may be distinctive from the target stimuli. For example, distraction stimuli may be a different colour, size, shape, location, appearance, brightness, texture, feel (such as degree of vibration), duration and/or temperature to the target stimuli. The distraction stimuli may be provided in a different modality to the target stimuli. The distraction stimuli may comprise visual and/or tactile and/or audible distraction stimuli.

The distraction stimuli may be provided during provision of target stimuli. The distraction stimuli may be provided between provision of target stimuli. The distraction stimuli may be provided both during and between target stimuli.

The method may comprise directing a user's attention to a predetermined location, for example a fixation point, for example before a trial begins.

The method may comprise providing a cue to a user, for example a cue that a target stimulus is to be provided. The cue may be such as to alert a user that a stimulus will be provided. The cue may comprise at least one visual and/or tactile and/or audible alert. The cue may be distinctive from the target stimuli. For example, the cue and/or the alerts produced thereby may be a different colour, size, shape, location, light source type, appearance, brightness, texture, feel (such as vibrating or not), duration and/or temperature to the target stimuli.

The method may comprise performing one or more operating procedures. An operating procedure may comprise providing a sequence of one or more target stimuli and/or delays and/or distractions. The operating procedures may be selectable from a plurality of operating procedures. The target stimuli and/or delays and/or distractions of each operating procedure may be selectable.

Each procedure may comprise presentation of a plurality of stimuli. Each operating procedure may comprise presentation of between 1 and 30 stimuli, optionally between 5 and 14 stimuli. At least one operating procedure comprising between 15 and 30 stimuli may be provided.

The method may comprise performing a test comprising a plurality of operating procedures. At least one operating procedure in the test may differ from at least one other operating procedure in the test. Each procedure may differ in the method of user response or input, for example, an audible response or a tactile response, such as pressing a button. Each procedure may differ in the distraction provided, for example in whether or not distraction is provided or the amount of distraction provided. Each procedure may differ in the number of stimuli producing means used. Each procedure may differ in the type of target stimuli used.

The method may comprise providing at least first and second target stimuli. The first and second target stimuli may be provided by different stimulus providing means. Determining a user's attention to the target stimuli may comprise determining a user's attention to at least both first and second target stimuli.

The method may comprise displaying the target stimulus for a duration of between 200 ms and 2000 ms, optionally between 600 ms and 1400 ms, further optionally for a duration substantially equal to 1000 ms.

The method may comprise providing a delay between target stimuli. The delay between target stimuli may be variable and/or random. The delay may be greater than 1000 ms. The delay may be between 800 ms and 4500 ms, optionally between 2050 and 4050 ms. The delay may be substantially equal to or greater than 3000 ms.

Each operating procedure may last for between 7 seconds and 180 seconds.

The user may provide a response to the target stimulus. The response may be a response providing information and/or observations based on the target stimuli.

The response may be an audible response to the target stimulus.

The method may comprise the monitoring the response of a user to an operating procedure. The response may be a number of times a target stimulus has been provided during the procedure.

The method may comprise the user providing at least one response during the procedure. The response may be a response to a target stimulus. The response may be provided using an input device. The response may comprise pushing a button.

The method may comprise providing a response time frame for responding to a target stimulus, wherein a response to a target stimulus is treated as valid if it is made within the response time frame. The response time frame for responding to a target stimulus may begin after the target stimulus is initiated, which may comprise a lag period between initiation of the target stimulus and the beginning of the response time frame. The response time frame for responding to a target stimulus may end after the target stimulus is no longer provided, which may comprise a further lag period between the end of provision of a stimulus and the end of the response time frame for responding to that stimulus. The lag time may be within the range 50 ms to 200 ms, and/or 100 ms to 150 ms. The further lag time may be within the range 50 ms to 1000 ms, and/or 100 ms to 500 ms. The time frame for responding to a stimulus may lie between 100 ms and 2000 ms from the start of the stimulus. The time frame may have a duration of between 500 ms and 2000 ms, and/or between 1000 ms and 1500 ms. The time frame for responding to a stimulus may lie in the range of 100 ms to 2000 ms from the start of the stimulus.

The method may comprise providing distraction stimuli during provision of the target stimuli. The apparatus may be adapted to provide the distraction stimuli between provision of target stimuli. The apparatus may be adapted to provide the distraction stimuli both during and between target stimuli.

Each distraction stimuli may be provided for a shorter time than the target stimuli.

Each distraction stimulus may be displayed for 200 ms or less, but may be longer depending on the nature of the task, for example in certain circumstances, it may be preferable to provide sustained flashing of distracters, or even sustained illumination for several seconds.

Each procedure may be arranged to last between 10 seconds and 120 seconds.

The method may comprise processing the responses of a user to the target stimuli to determine a measure of sustained attention for a user. The method may comprise determining a respective measure of sustained attention from the responses obtained for each operating procedure. The measure of sustained attention may also be referred to as a measure of sustained inattention.

The method may comprise combining the determined measure of sustained attention for each operating procedure of a test to obtain a combined measure of sustained attention for the test. Alternatively, or additionally the method may comprise processing the responses obtained for each operating procedure together to obtain the measure of sustained attention.

The method may comprise determining the measure of sustained attention in dependence on at least one of the presence or absence of a response to at least one stimulus; the correctness of the response to at least one stimulus; the timing of the response (for example delay in responding to) to the at least one stimulus; the variation during the duration of a test in the presence or absence of response and/or the correctness of response and or the timing of response.

The method may comprise determining a measure of sustained attention of the user, which may comprise comparing the number of valid responses with correlation data.

The method may comprise comparing the determined measure to a threshold and providing an output in dependence on whether the determined measure is greater than the threshold.

The method may comprise using the measure of sustained attention of the user to determine a measure of delirium in the user. The method may comprise comparing the measure of sustained attention of the user with a threshold and determining whether or not delirium is present in the user dependent on whether the measure of sustained attention of the user is above or below the threshold.

According to another aspect of the invention is a method of operating a testing apparatus according to the first aspect comprising providing one or more target stimuli using the stimulus providing means such that a user's sustained attention to the stimuli can be determined.

According to a further aspect of the present invention is a method of determining a measure of delirium, comprising determining a measure of sustained attentional performance using the method of the second or third aspects and/or the apparatus of the first aspect, and determining a measure of delirium using the measure of sustained attentional performance.

According to a another aspect of the present invention is a method of determining a measure of attention comprising providing a plurality of visual stimuli, counting the visual stimuli, comparing the number of visual stimuli counted with the number of visual stimuli presented and determining a measure of attention therefrom.

The method may comprise providing each stimuli for between 100 ms and 5000 ms, or between 200 ms and 2000 ms, preferably between 600 ms and 1400 ms and most preferably substantially 1000 ms. The method may comprise providing a delay of at least 2000 ms between stimuli. The method may be arranged such that each procedure has a duration of between 10 seconds and 120 seconds.

According to another aspect of the present invention is a computer program product for operating the apparatus of the first aspect or performing the method of any of the second to fifth aspects.

According to a further aspect of the present invention is an apparatus or data carrier when programmed or containing the computer program product of the fifth aspect.

The apparatus may comprise a computer.

In further independent aspects of the invention there may be provided an apparatus or method substantially as described herein with reference to the accompanying drawings.

Any feature in one aspect of the invention may be applied to other aspects of the invention, in any appropriate combination. For example, apparatus features may be applied to method features and vice versa.

DESCRIPTION OF THE DRAWINGS

Various aspects of the invention will now be described by way of example only and with reference to the accompanying drawings, of which.

SPECIFIC DESCRIPTION

Figure 1:
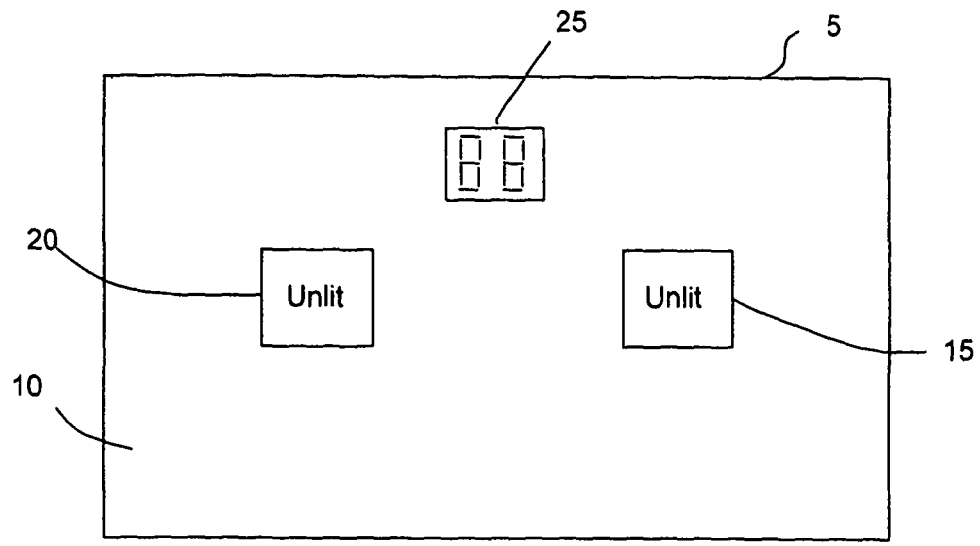
FIG. 1 is an apparatus for determining sustained attentional performance according to a first aspect of the present invention, the apparatus being in an unlit configuration.

FIGS. 1 to 4 show a test apparatus in the form of a portable battery-powered device 5 that is operable to implement a series of simple sustained visual attention tasks that do not require rapid stimulus processing or responding. The device 5 comprises a housing 10 and a stimulus provider in the form of two lightable buttons 15, 20, the buttons 15, 20 being located on either side of an LED display 25. The buttons 15, 20 are provided on a plain surface of the device. In the embodiment of FIG. 1, the housing 10 is formed of metal or plastic and has dimensions of around 20 cm by 5-7 cm by 12-15 cm, but any suitable material and suitably-sized housing may be used.

Figure 4:
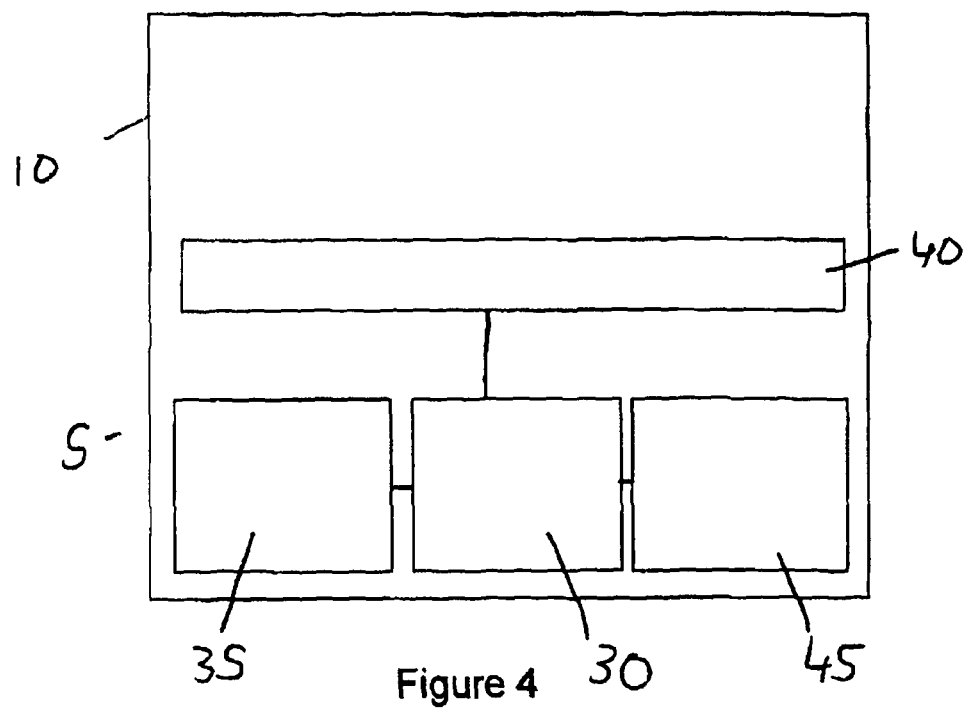
FIG. 4 is an internal schematic of components of the apparatus of FIG. 1.
Figure 5A:
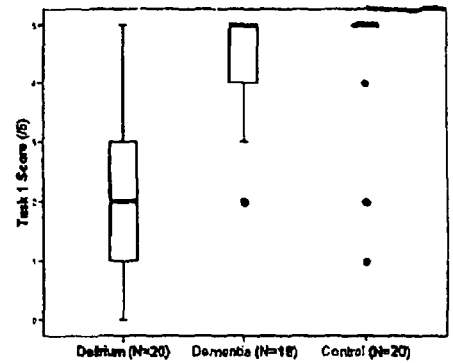
FIGS. 5(a) to (h) are box-plots showing the results of 8 tasks performed using the apparatus of FIG. 1.
Figure 5B:
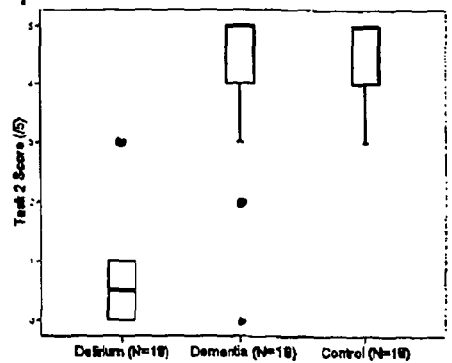
Figure 5C:
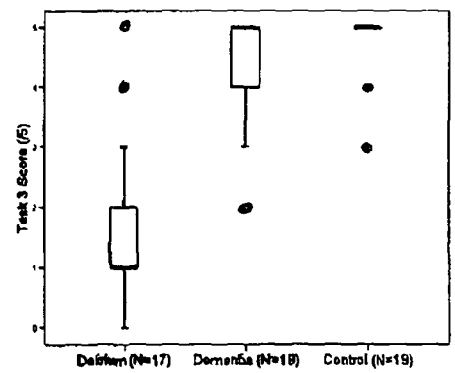
Figure 5D:
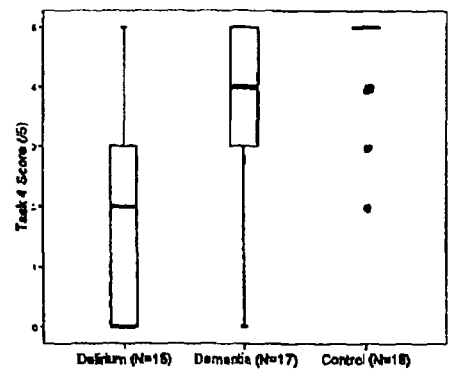
Figure 5E:
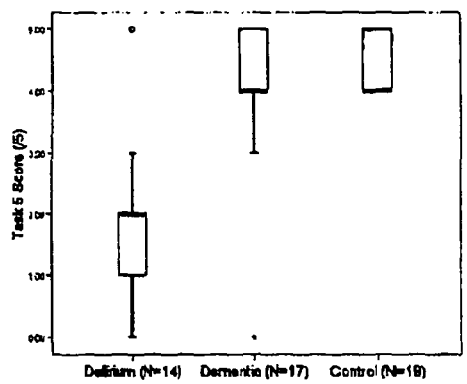
Figure 5F:
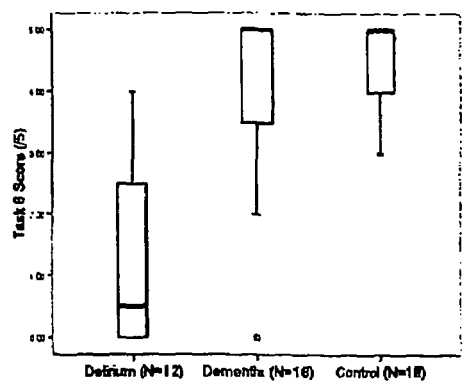
Figure 5G:
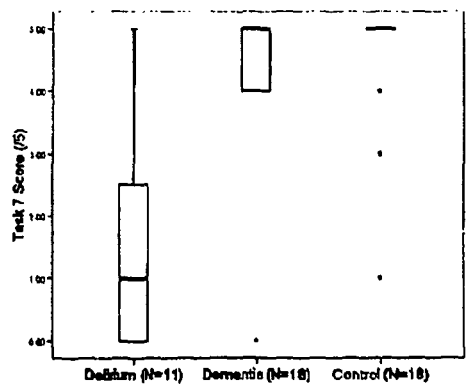
Figure 5H:
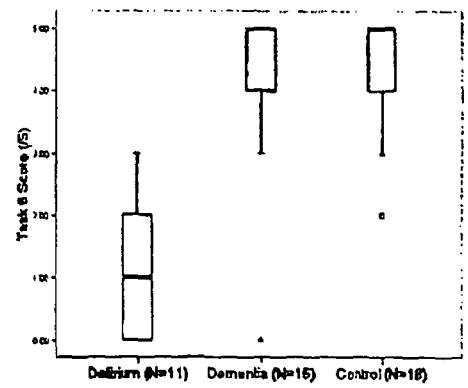

As shown in FIG. 4, the device 5 also comprises a processor 30 for controlling operation of the device 5 and processing measurements, a memory 35 for storing data, a driver 40 controllable by the processor 30 for operating the LED display and the lightable buttons 15, 20, and a communications unit 45 for communicating with a computer (not shown) to allow programming of the device 5. The communications unit may comprise a standard interface for communicating with a PC or other computer, for example a USB port. The processor 30 and associated system may be, for example, based around a PIC microcontroller and a custom designed Printed Circuit Board (PCB).

Figure 2:
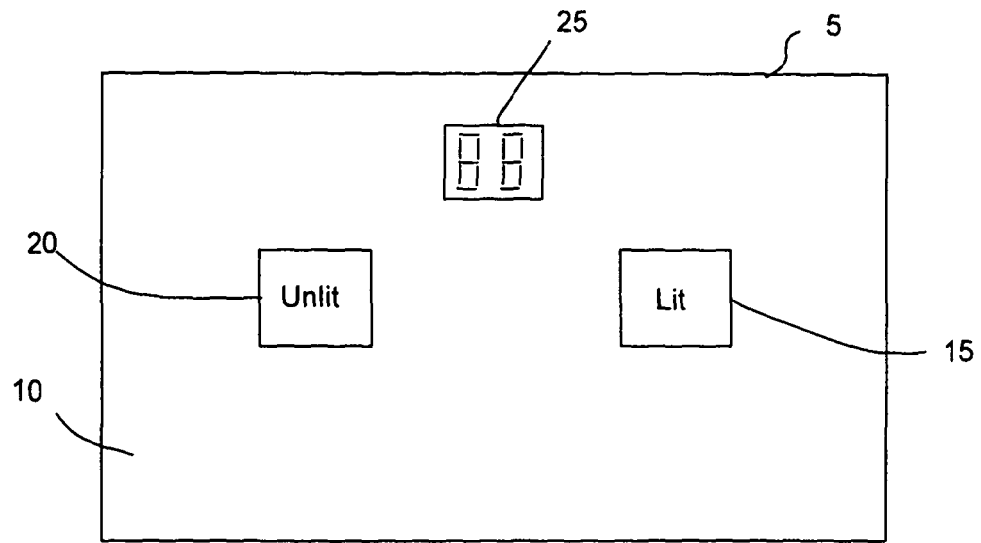
FIG. 2 is an apparatus for determining sustained attentional performance according to a first aspect of the present invention, the apparatus being in a lit configuration.
Figure 3:
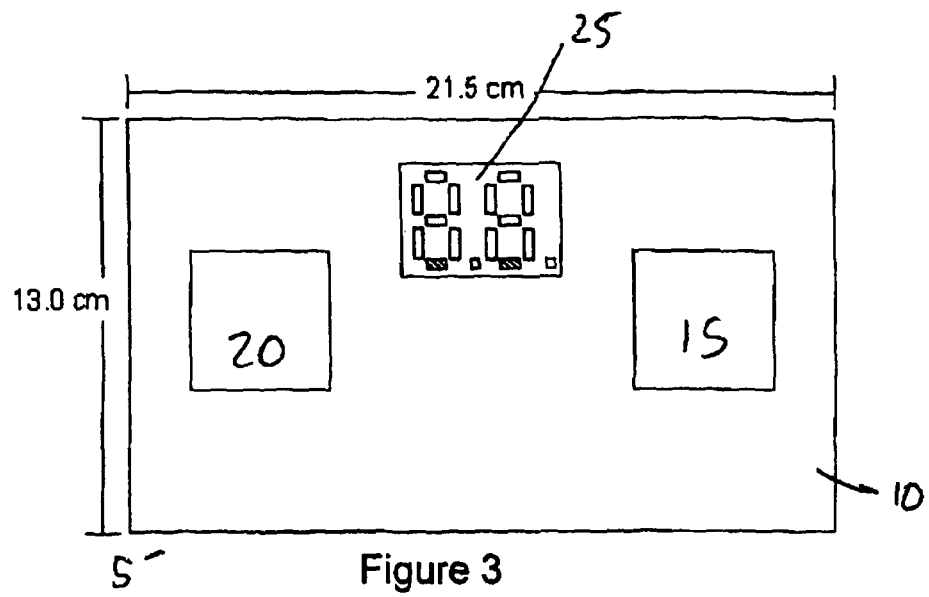
FIG. 3 is a schematic of the apparatus of FIG. 1.

Each button 15, 20 covers a respective light source (not shown), such as an LED or bulb for lighting the respective button 15, 20. The light sources 15, 20 may be LEDs, due to the improved response times over bulbs, which allows better correlation of intended and actual illumination times. The lightable buttons 15, 20 are formed from a opalescent material, which in this embodiment is non-coloured. In this way, when the respective light source is lit, the respective button 15 appears lit, as shown in FIG. 2. When the respective light source is unlit, the button 15, 20 appears solid and the light source is not visible, as shown in FIG. 1. The lighting of the light sources is controllable by the processor 30 via the driver 40.

Each button 15, 20 comprises a switch (not shown) for determining whether a button 15, 20 has been operated by a user. Each switch is in communication with the processor 30 in order to relay operation of the buttons 15, 20 to the processor 30. The buttons and switches can be configured so that they are fairly light to press and easy to use by frail older patients without much strength and/or patients who may have joint abnormalities, but so that a positive pressure is required to trigger them (for example more pressure than just resting a finger on a button).

The LED display 25 is operable under control of the processor 30. Selective display segments of the LED display 25 may be lit in red. Optionally, the LED display 25 is also covered by an opalescent cover in order to hide the LED display 25 when unlit. Depending on the pattern of segments lit, the LED display 25 is operable to display text or numbers on non-textual patterns.

The device 5 can also include an operator interface on a rear face (not shown) of the device that usually comprises set of push buttons or an alphanumeric interface, that are operable by an operator to switch the device on and off and to select and initiate a desired test that comprises a sequence of target stimuli.

The processor is operable to light the buttons 15, 20 at appropriate time intervals in order to provide target stimuli, which the user must use to complete a task. The processor is also operable to light the LED display to provide distractions and to display information, such as a number of valid responses. The number, timing and form of the stimuli provided by the lightable buttons 15, 20, as well as the number timing and form of any distractions is programmable into the processor 30.

The processor 30 is optionally operable to monitor responses from a user in the form of respective button 15, 20 presses to the or each target stimulus. The processor is operable to associate a response time window with provision of each stimulus, wherein a response is recorded as valid if the response to a stimulus is provided within the response window. Valid responses are stored in the memory. It will be appreciated that the device may be programmed to not require and or collect responses, which may instead by given using other channels, for example, verbally.

The processor 30 may be configured to process the responses to determine a measure of sustained attention in dependence on at least one of the presence or absence of a response to at least one stimulus; the correctness of the response to at least one stimulus; the timing of the response (for example delay in responding to) to the at least one stimulus; the variation during the duration of a test in the presence or absence of response and/or the correctness of response and or the timing of response. Alternatively or additionally, response data can be transferred from the device to a PC or other computer and the processing of the responses can be performed by processing software at the PC or other computer. In the case of counting tests, a user can tell an operator a count number after a test, and the operator can manually enter the count number into the PC or other computer for processing.

In one mode of operation, the processor 30, PC or other computer determines the number of valid responses obtained from a user for a particular operating procedure, also referred to as a task, and determines a measure of sustained attention from the number of valid responses by comparing the number of valid responses with data stored in a lookup table. The data stored in the lookup table correlates task scores with values of a measure of sustained attention.

The correlation data is usually derived from a calibration procedure for that task, in which the task is performed by a number of reference subjects using the device 5. The reference subjects also perform known testing procedures and the scores achieved using the device are correlated with the outcome of the other testing procedures. In one example, the scores obtained by the reference subjects upon performing the tasks using the device are correlated with the outcome of standard tests for the presence or absence of delirium (for example, the Confusion Assessment Method and Delirium Rating Scale-Revised 98 (DRS-R-98) and the Mini-Mental State Examination). Correlation data representing the correlation between the task scores and the presence or absence of delirium determined using the known tests for delirium are stored, and can be subsequently used to correlate scores obtained by patients with a measure of the likelihood of the presence of delirium. In one mode of operation, a threshold indicator of the presence of delirium is stored, and if a patient obtains a score less than or equal to the threshold then the processor 30, PC or other computer provides an output signal indicating that delirium may be present.

The processor 30 or the PC or other computer is operable to compare the determined measure of inattention to the or a threshold and to provide an output in dependence on whether the determined measure of inattention is greater than the threshold. The output may comprise an indication that, for example, delirium may be present and that further examination of a patient for delirium may be required.

The device 5 is optionally sealed, for example within an elastomeric coating, which allows easy cleaning of the device and prevents ingress of dirt or infectious agents and protects the internal electronics of the device 5. Optionally, the device is arranged to receive and/or be fixable to a transparent plastic cover, which may be a single use/disposable cover, which allows the patient to see the stimuli but at the same time prevents ingress and transmission of infectious agents.

The device 5 is portable, robust, durable, easily handled by staff and patients, and has acceptable battery and power life, able to provide flashing sequences/lights that are obvious, with no inconsistencies between the strength of the sequences flashing and their speed, unless designed to do so for the purpose and provides lights and buttons that are clearly identifiable by patients.

The device 5 may be designed, for example by shaping of edges and selection of surface and interior materials used, so that the device is not conducive to pathogen growth (eg: MSRA), and is easily cleaned. The device 5 is programmable, has a PC based interface, enhanced data storage and enhanced lights for distracters and cueing.

Optionally, the apparatus comprises an illuminable fixation point (not shown) shaped as a cross, centrally mounted on the device between the two lightable buttons 15, 20. The illuminable fixation point is provided with an opalescent cover so that the illuminable fixation point is hidden when unlit but becomes visible when lit.

As a further option, the apparatus comprises a cueing means for example in the form of a cueing device (not shown) for warning a user in advance that a stimulus will be provided. In optional embodiments, the or each cueing device is located at or adjacent a lightable button 15, 20, for example in the form of four red LEDs at each corner of each lightable button 15, 20. The four LEDs can be any suitable colour, but usually they are a different colour to the colour of the lightable buttons when lit. In an optional embodiment, the cueing are combined with the fixation point, for example, the fixation point comprises two arrows, one arrow pointing to each lightable button.

The cues provided by the cueing device are distinctive from the target stimuli. For example, the cueing device may comprise differently coloured and sized lights to the lightable buttons.

The device is operable to provide a warning to a user by illuminating a cueing device associated with a particular lightable button shortly before the lightable button is illuminated. For example, the four LEDs at the corner of a lightable button or the arrow pointing to the button may be illuminated shortly before the button is lit. Additionally, or alternatively, further LEDs or other cueing devices can be provided in positions not associated with particular ones of the buttons, for example positioned around a central location and/or around both buttons, to provide for a neutral cueing mechanism not associated with a particular one of the buttons.

Optionally, the processor is adapted to determine a reaction time and/or average reaction time, which may be storable in a memory. The reaction times may be usable in conjunction with the cueing device in order to determine the effects of endogenous attention shifts, as a user who has moved their attention to a stimulus providing device before the target stimulus is provided may be expected to give a faster response to the target stimulus.

A number of examples of tests that can be performed by the device 5 are described below. The test examples require one or more of the following: (a) effortful sustaining of visual attention with stimulus gaps of more than 2 seconds, (b) retention of task instructions, (c) maintaining a running total of the number of lights, (d) absence of complex cognitive processing, (e) in some cases having to monitor the presence of distracters, and (f) in some cases having to monitor differing stimuli, for example, stimuli occurring at more than one location.

The core cognitive deficit in delirium is inattention (also known by the term 'attentional deficits'). However, the concept of attention is complex. One description is, "attention is a complex system of interacting components that allows the individual to filter relevant and irrelevant information in the context of internal drives and intentions, hold and manipulate mental representations, and monitor/modulate responses to stimuli". The device is operable to perform tasks that involve several elements of attention, for example as described in the preceding paragraph, and that may thus be sensitive to delirium. However, the main aspect that is tested is sustained visual attention by means of counting stimuli with relatively long gaps (for example, greater than 2 seconds) between these stimuli.

The processor is operable for implementing one or more sustained attention tasks or operating procedures to be performed by the user. In this example, eight sustained attention tasks are performed, although it will be appreciated that the number of tasks performed may vary.

The tasks are editable and programmed into the processor and memory using a computer via the communications module.

Each task comprises lighting up the buttons 15, 20 for specified periods. Delays are provided between each button 15, 20 lighting event. Depending on the programming of the task, either only one of the buttons 15, 20 or either of the buttons 15, 20 may be lit in order to provide a stimulus event. Furthermore, depending on the programming of the task, the processor 30 is operable to light portions of the LED display 25 in order to provide distraction stimuli.

In some tasks, the processor 30 may be programmed to ignore responses detected by the buttons 15, 20, for example if the task is to try to remember the number of times a button 15, 20 was lit, and verbally reporting to an operator at the end of the task. For some tasks, the processor 30 may be programmed to detect operation of appropriate buttons 15, 20 in response to provision of a stimulus event involving lighting of a button 15, 20.

In this way, the device is programmable to selectively provide a variety of stimulus events, a variety of distraction stimuli and optionally determine responses to the stimulus events.

The use of the device 5 as part of a method for assessing delirium in patients is described. The method comprises using the device 5 in order to set eight attention tasks to be performed by a patient.

The first four attention tasks all require patients to verbally report how many times the buttons 15, 20 on the device 5 were illuminated during each task.

In task 1 (simple slow counting task—no response), the device 5 is placed in portrait orientation in front of the patient. The patient is instructed to keep watching the button 15, 20 that is located closest to them, and to count how many times it is lit up. Once the patient indicates that they understand what they have to do, the trial is started. One of the buttons 15, 20 is then illuminated for between 3 and 14 times in each trial. All illuminations are colourless and last for 1000 ms. The duration of the intervals between the illuminations are varied within the range of 2050 to 4050 ms. The end of each trial is signalled to an experimenter by a small red dot illuminating on the LED display. The experimenter asks the patient to report how many times the button 15, is illuminated. The task was scored from 0-5 according to the number of correct responses given.

During task one, the processor 30 is operable to implement 6 trial blocks. The first block is an unscored practice block that may be repeated if required. Each block starts when the experimenter presses one of the buttons. The processor 30 undergoes a 1000 ms delay before the trials start.

Each trial contains the following steps.
(1) Each trial begins with a delay in the range of between 50 and 2050 ms (in 16 steps of 125 ms). The length of the delay is randomly determined for each trial. However, the list of delays can be programmed so that it is subsequently fixed for all participants.
(2) The processor 30 illuminates button 15 for 1000 ms then switches the illumination off.
(3) The processor 30 implements a delay of 2000 ms.
(4) The next trial begins with Step 1.

The final trial in each block ends after completion of step 3. The processor 30 is arranged to indicate the end of the block to the experimenter by constantly illuminating dot point segments of LED display 25. The experimenter then presses button 15 once to turn off the illumination of the LED dot point segments. The experimenter then presses button 15 again to begin the next block of trials.

Each subsequent block of the first task contains an increasing number or blocks. In this example, block one contains 3 trials, block two contains 5 trials, block three contains 8 trials, block four contains 7 trials, block five contains 10 trials and block six contains 14 trials.

Task 2 (slow counting with distracters—no response) is similar to task 1 but with the addition of irrelevant distracting stimuli being presented by illumination of the LED display 25 during the majority of trials. These distracting stimuli comprise series of 4 or 8 alternating red flashes of two segments of the LED display 25. Each flash lasts 200 ms and there is no interval between the flashes in each distracting stimulus. The processor 30 is operable to present distracting stimuli at various time-points within each trial, with some distracting stimuli occurring at the same time as a target illumination, and others occurring between target illuminations. The distracting stimuli are selected so as to be clearly different to the target button 15, 20 flashes, and also to be difficult to count as discrete events. Patients are informed about the presence of these distracting stimuli before beginning the task, and are instructed to ignore them.

The processor 30 implements the procedure of task two in 6 trial blocks. Each block starts when experimenter presses button 20. The processor 30 then implements a 1000 ms delay before the trials start.

Each trial contains the following steps:
(1) Each trial begins with the processor 30 implementing a first delay in the range of between 50 and 2050 ms (in 16 steps of 125 ms) (which is generally randomly determined but may be programmed so as to be fixed);
(2) The processor 30 illuminates button 15 for 1000 ms then turns the illumination off. In one third of the trials the processor 30 illuminates segments of the LED display 25 in order to present a distracting stimulus during this period in which the button 15 is illuminated.
(3) The processor 30 then implements a second delay of 2000 ms. During the delay, the processor 30 may operate the LED display 25 to present a variable amount of distracting stimuli in the form of flashes of illumination from segments of the LED display 25. In this example, no (in 25% of trials), one (in 50% of trials), or two (in 25% of trials) distracting stimuli are presented. Where one distracting stimulus occurs, this occurs with equal probability in the $1^{st}$ and $2^{nd}$ second of this delay period.
(4) The next trial begins with Step 1.

Each distracting stimuli comprises a 200 ms delay, followed by a 200 ms flash of a first LED display 25 segment, a 200 ms flash of a second LED display 25 segment, another 200 ms flash of the first LED display 25 segment and another 200 ms flash of the second LED display 25 segment.

The final trial in each block ends after completion of step 3. The processor 30 indicates the end of the block to the experimenter by the constant illumination of dot point segments of LED display 25. The experimenter then press button 20 once to turn off the illumination of the LED dot point segments. The experimenter may then press button 20 again to begin the next block of trials.

The blocks of the procedure of the second task contain the following number of trials: block one contains 4 trials, block two contains 5 trials, block three contains 6 trials, block four contains 11 trials, block five contains 9 trials and block six contains 13 trials.

For task 3 (dual location simple slow counting task—no responses), the device 5 is positioned in landscape orientation in front of the participant. The task is similar to task 1 except that, for task 3, either of the two buttons 15, 20 can be illuminated on each occasion. Patients are informed before starting the task that either button 15, can light up on each occasion, and instructed to count the total number of illuminations.

The processor 30 is operable to run task three in 6 trial blocks with the following structure:

Each block starts when experimenter presses button 20, whereupon, the processor 30 implements a 1000 ms delay before trial blocks start. Each trial block contains the following steps:
(1) The processor 30 begins each trial by implementing a delay of between 50 and 2050 ms (in 16 steps of 125 ms) (the delay may be randomly determined or programmed to be fixed).
(2) The processor 30 then illuminates either button 15 or button 20 for 1000 ms then turns the illumination off. Button 15 and button 20 are illuminated a fixed number of times within each block. The order in which the two buttons 15, 20 are illuminated within each block is randomly determined for the first patient then fixed.
(3) The processor 30 then implements a delay of 2000 ms.
(4) The next trial begins with Step 1.

The final trial in each block ends after completion of step 3. The end of the block is indicated to the experimenter by the constant illumination of dot point segments of the LED display 25. The experimenter then presses button 20 once to turn off the illumination of the LED dot point segments. The experimenter then presses button 20 again to begin the next block of trials.

Table 1 below shows number of flashes from each button performed in each block.

TABLE 1

| Block | Total number of trials | Number of Button 20 flashes | Number of Button 15 flashes |
|---|---|---|---|
| Block 1 | 4 | 2 | 2 |
| Block 2 | 5 | 3 | 2 |
| Block 3 | 7 | 3 | 4 |
| Block 4 | 6 | 3 | 3 |
| Block 5 | 12 | 7 | 5 |
| Block 6 | 14 | 6 | 8 |

Task 4 (dual-location simple slow counting task with distracters—with no responses) is similar to task 3 but with the addition of the same type of distracting stimuli presented in task 2.

The processor 30 is operable to control performance of task four in 6 trial blocks. Each block starts when experimenter presses button 20, whereupon the processor 30 implements a 1000 ms delay before trials start.

Each trial contains the following steps:
(1) Each trial begins with a delay of between 50 and 2050 ms (in 16 steps of 125 ms). This is determined randomly then programmed to be fixed.
(2) The processor then illuminates button 15 or button 20 for 1000 ms then switches the illumination off. Button 15 and button 20 are illuminated a fixed number of times within each block, as detailed in Table 2. The order in which the two buttons 15, 20 are illuminated within each block is randomly determined and then programmed to be fixed. The processor 30 is operable to provide a distracting stimulus during the button illumination period in trials, and with equal probability during button 15 or 20 illumination. The distracting stimulus is as described above in relation to task 2.
(3) The processor 30 implements a delay of 2000 ms. During the delay, the processor 30 may illuminate the LED in order to provide distracting stimuli. No distracting stimuli are provided in 25% of the trials, one distracting stimulus is provided in 50% of the trials and two distracting stimuli are provided in 25% of the trials. Where 1 distracting stimulus occurs, this occurs with equal probability in the $1^{st}$ and $2^{nd}$ second of this delay period. The distracting stimuli are as described above in relation to task 2.
(4) The next trial begins with Step 1.

The final trial in each block ends after completion of step 3. The end of the block is indicated to the experimenter by constant illumination of dot point segments of the LED display 25. The experimenter then presses button 20 once to turn off the illumination of the LED dot point segments. The experimenter then presses button 20 again to begin the next block of trials.

Table 2 shows the number of flashes of each button in each block.

TABLE 2

| Block | Total number of trials | Number of Button 20 flashes | Number of Button 15 flashes |
|---|---|---|---|
| Block 1 | 3 | 2 | 1 |
| Block 2 | 6 | 3 | 3 |
| Block 3 | 8 | 3 | 5 |
| Block 4 | 7 | 4 | 3 |
| Block 5 | 10 | 6 | 4 |
| Block 6 | 13 | 6 | 7 |

The stimuli in tasks 5-8 follow the same patterns as for tasks 1-4. However, instead of verbally counting the number of illuminations, patients are required to press a button 15, 20 each time a button 15, 20 is illuminated. In these tasks the buttons 15, remain illuminated for 1000 ms or until they are pressed by the participant. Any button 15, 20 press occurring within the period of 100 to 2000 ms of a button 15, 20 being illuminated is counted as a valid response and stored in the memory, thus allowing responses made up to 1000 ms after a target illumination is presented to be counted as correct. Any button 15, 20 presses made outside of this time window, or additional button 15, 20 presses made to the same target stimulus, are recorded but classed as being invalid. At the end of trial the number of valid and total (i.e. valid+invalid) responses is displayed in the central display and recorded by the experimenter. The trial is scored as correct if the correct number of valid responses had been made, resulting in a possible score of 0-5 for each task.

The operation of the device during tasks five to eight is as follows:

Task 5: (Simple manual response task with button responses)

The processor 30 is operable to implement 6 trial blocks.

Each block is started by operation of button 20. The processor 30 implements a 1000 ms delay before the trials start. Each trial contains the following steps:
(1) The processor 30 implements a delay of between 50 and 2050 ms (in 16 steps of 125 ms) before each trial begins;
(2) The processor 30 then illuminates button 15 for 1000 ms (or until pressed) then switches it off. If button 15 is validly pressed then the valid response is recoded in the memory and the light stays unilluminated for the remaining duration of the 1000 ms;
(3) The processor 30 then implements a delay of 2000 ms; and
(4) The next trial begins with Step 1.

The final trial in each block ends after completion of step 3. The end of the block is indicated to the experimenter by the constant illumination of dot point segments of the LED display 25. The experimenter then presses Button 20 once to turn off the illumination of the LED dot point segments.

The experimenter then presses button 20. The processor 30 is then operable to retrieve the number of trials that were followed by a valid button 15 or button 20 press in the 100-2000 ms window after the onset of button 20 being illuminated from the memory 35 and display this on the LED display 25. The experimenter then presses button 20 again, whereupon the processor 30 retrieves the total number of times that button 15 or button 20 was pressed during the block from the memory and displays this on the LED display 25. The experimenter then presses button 20 again, whereupon, the processor 30 is operable to clear the LED display. The experimenter then presses button 20 again to begin the next block of trials.

The blocks of task 5 contain the following number of trials: block one contains 4 trials, block two contains 5 trials, block three contains 8 trials, block four contains 7 trials, block five contains 10 trials and block 6 contains 14 trials.

Task 6 (manual response task with distracters—with button responses)

The processor 30 implements task six in 6 trial blocks. Each block starts when experimenter presses button 20. The processor 30 then implements a 1000 ms delay before trials start. Each trial contains the following steps:

(1) Each trial begins with a first delay of between 50 and 2050 ms (in 16 steps of 125 ms). The delay is initially randomly determined and then programmed so as to be fixed.

(2) The processor 30 is the operable to illuminate button 15 for 1000 ms (or until pressed) and then turn the illumination off. If button 20 is validly pressed then the valid response is recorded in the memory and the light stays unilluminated for the remaining duration of the 1000 ms. The processor 30 is operable to illuminate the LED display 25 in order to provide a distracting stimulus in a third of the trials. The distracting stimuli are implemented as described in relation to Task 2.

(3) The processor 30 then implements a second delay of 2000 ms. During the delay, the processor 30 implements a variable number of distracting stimuli. In this example, the processor 30 implements no distracting stimuli in 25% of trials, one distracting stimulus in 50% of trials and two distracting stimuli in 25% of trials. Where one distracting stimulus is provided, this occurs with equal probability in the $1^{st}$ and $2^{nd}$ second delay. The distracting stimuli are implemented as described above in relation to task 2.

(4) Next trial begins with Step 1

The final trial in each block ends after completion of step 3. The end of the block is indicated to the experimenter by constant illumination of dot point segments of the LED display 25. The experimenter then presses button 20 once to turn off the illumination of the LED dot point segments. The experimenter then presses button 20 to display the collected data. The processor 30 then accesses the memory to retrieve the number of trials that were validly followed by a button 15 or button 20 press within the 100 to 2000 ms window after the onset of button 15 being illuminated and display this using the LED display 25. The experimenter then presses button 20 again. The processor 30 is then operable to access the memory to retrieve the total number of times that button 15 or button 20 was pressed during the block and display this on the LED display 25. The experimenter then presses button 20 again to clear the LED display 25.

A further press of button 20 begins the next block of trials.

The blocks of the sixth test contain the following number of trials: block one contains 3 trials, block two contains 5 trials, block 3 contains 7 trials, block 4 contains 10 trials, block 5 contains 9 trials and block 6 contains 13 trials.

Task 7 (dual-location manual response task with button responses)

The processor 30 implements task 7 in 6 trial blocks. Each block starts when the experimenter presses button 20, whereupon the processor 30 implements a 1000 ms delay before the trials start. Each trial contains the following steps:

(1) Each trial begins with the processor 30 implementing a first delay of between 50 and 2050 ms (in 16 steps of 125 ms). The delay time is initially determined randomly then programmable to be fixed in subsequent trials.

(2) The processor 30 illuminates button 15 or button 20 for 1000 ms (or until either button 15, 20 is pressed) then turns the illumination off. If either button 15, 20n is validly pressed then the valid response is stored in the memory and the light stays unilluminated for the remaining duration of the 1000 ms. Button 15 and button 20 are illuminated a fixed number of times within each block, as shown in table 3. The order in which the two buttons 15, 20 are illuminated is initially randomly determined and then subsequently is programmable so as to be fixed.

(3) The processor 30 then implements a second delay of 2000 ms.

(4) The next trial begins with Step 1

The final trial in each block ends after completion of step 3. The end of the block is indicated to the experimenter by constant illumination of the dot point segments of LED display 25. The experimenter then presses button 20 once to turn off the illumination of the LED dot point segments. The experimenter then presses button 20, whereupon the processor 30 is operable to access the memory and retrieve the number of trials that were followed by a valid press of button 15 or button 20 in the 100 to 2000 ms window after the onset of either button 15, 20 being illuminated, and display this using the LED display 25. The experimenter then presses button 20 again, whereupon the processor 30 is operable to access the memory and retrieve the total number of times that button 15 and button 20 were pressed during the block and display this using the LED display 25. The experimenter presses button 20 again to clear the LED display and pressing button 20 again begins the next block of trials.

Table 3 shows the number of flashes from each Button.

TABLE 3

| Block | Total number of trials | Number of Button 20 flashes | Number of Button 15 flashes |
| --- | --- | --- | --- |
| Block 1 | 4 | 2 | 2 |
| Block 2 | 6 | 4 | 2 |
| Block 3 | 7 | 3 | 4 |
| Block 4 | 11 | 6 | 5 |
| Block 5 | 8 | 4 | 4 |
| Block 6 | 12 | 5 | 7 |

Task 8: (dual-location manual response task with distracters and button responses)

The processor 30 is operable to implement task 8 in six trial blocks. Each block starts when the experimenter presses button 20, whereupon the processor 30 implements a 1000 ms delay before the trials start. Each trial contains the following steps:

(1) Each trial begins with the processor 30 implementing a first delay of between 50 and 2050 ms (in 16 steps of 125 ms). The delay duration is initially randomly determined then subsequently programmed to be fixed.

(2) The processor 30 is then operable to illuminate. button 15 or button 20 for 1000 ms (or until either button 15, 20 is pressed) then turn the illumination off. If either button 15, 20 is pressed then a valid response is logged in the memory and the light remains unilluminated for the remaining duration of the 1000 ms. Button 15 and Button 20 are illuminated a fixed number of times within each block, as shown in Table 4. The order in which the two buttons 15, 20 are illuminated within each block is initially randomly determined and then subsequently programmed to be fixed. The processor 30 is operable to implement a distracting stimulus during this period in which one of the buttons 15, 20 is illuminated in 1 out of every three trials, and with equal probability during button 15 or button 20 illumination.

(3) The processor 30 is operable to implement a second delay of 2000 ms, The processor 30 is operable to implement variable distracting stimuli during the delay. In this example, the processor 30 is operable to implement no distracting stimuli in 25% of the trials, one distracting stimulus in 50% of the trials and two distracting stimuli in 25% of the trials. Where one distracting stimulus occurs, this occurs with equal probability during the $1^{st}$ and $2^{nd}$ second delays. The distracting stimuli are implemented as described above in relation to task 2.

(4) Next trial begins with Step 1.

The final trial in each block ends after completion of step 3. The end of the block is indicated to the experimenter by the constant illumination of the dot point segments of the LED display 25. The experimenter then presses button 20 once to turn off the illumination of the LED dot point segments. The experimenter then presses button 20 to display the data from the memory. The processor 30 retrieves the number of trials that were followed by a valid press of button 15 or button 20 in the 100 to 2000 ms window after the onset of either button 15, 20 being illuminated and displays this using the LED display 25. The experimenter then presses button 20 again, whereupon the processor 30 is operable to access the memory to retrieve the total number of times that the buttons 15, 20 were pressed during the block. The experimenter then presses button 20 again to clear the LED display 25 and presses button 20 again to begin next block of trials.

Table 4 shows the number of flashes from each button provided during each block.

TABLE 4

| Block | Total number of trials | Number of Button 20 flashes | Number of Button 15 flashes |
|---|---|---|---|
| Block 1 | 3 | 1 | 2 |
| Block 2 | 5 | 3 | 2 |
| Block 3 | 8 | 4 | 4 |
| Block 4 | 6 | 4 | 2 |
| Block 5 | 12 | 5 | 7 |
| Block 6 | 13 | 6 | 7 |

All eight vigilance tasks consist of one unscored practice trial followed by five scored trials. Practice trials are repeated, and additional clarification provided, for patients who respond incorrectly to the practice trial. Task instructions are also repeated between trials when necessary.

The apparatus and methods described above were used in a study to determine their effectiveness as a tool to assist in the diagnosis of delirium.

Three groups of patients were recruited for this study. These were: 1) patients with current delirium and no known dementia, 2) patients with dementia and no current delirium, and 3) cognitively normal (control) patients with no known dementia and no current delirium. As both delirium and dementia are associated with older age, only patients aged over 65 years were approached to take part. Exclusion criteria for all patients were visual or auditory impairments severe enough to affect the reliability of the cognitive testing, and the inability to provide informed consent.

Twenty patients with delirium were recruited from acute medical and surgical wards of a general hospital. Potential participants were first identified by ward staff, who named eligible patients who had shown evidence of an acute change in cognitive function since being admitted. In order to provide a comparison, the presence of delirium was formally assessed by a trained researcher using the Confusion Assessment Method (CAM), as described by Inouye et al. in "Clarifying confusion: the Confusion Assessment Method. A new method for detection of delirium." *Ann Intern Med* 113: 941-948 (1990). This diagnostic algorithm records the presence of the four core symptoms of delirium: 1) attentional impairment, 2) confused thinking, 3) disturbed consciousness, and 4) an acute onset or fluctuating course of symptoms. A diagnosis of delirium requires that symptoms 1 and 4, and either 2 or 3 are present.

The CAM criteria were evaluated using a validated battery of other techniques known in the art such as the MMSE, the Delirium Symptom Interview, and attentional assessments that required the patient to repeat strings of numbers in a forward or reverse order, and to list the days of the week and the months of the year backwards, as described in Simon, 2006 1662/id. Hospital staff and patients' medical notes provided additional diagnostic information.

Eighteen Dementia patients were recruited from a hospital outpatient memory clinic. All dementia patients had been diagnosed by a geriatrician as having either Alzheimer's dementia or mixed Alzheimer's and vascular dementia according to ICD-10 criteria as described in ICD-10: The ICD-10 Classification of Mental and Behavioural Disorders: Clinical Descriptions and Diagnostic Guidelines, 1992, World Health Organization.

Cognitively normal (control) patients were recruited from, and tested in, the same hospital wards as the patients with delirium. Patients were included if they had no evidence of dementia or delirium, as judged by the delirium assessments, their medical history, and their scores on the MMSE (using a cut-off score of 24/30). Three patients were subsequently excluded from this group for not meeting these criteria, resulting in a final group size of 20.

The presence of delirium was assessed in all patients using the assessment battery described above. The severity of delirium symptoms was also assessed in all patients using the Memorial Delirium Assessment Scale (MDAS) as described in Breitbart, 1997 1599/id. This comprises of a list of 10 common features of delirium, each of which are rated on a scale of 0-4 according to their presence and severity. The range of possible scores for the scale is therefore 0-40, with higher scores indicting more severe symptoms. Importantly, patients' performance on the vigilance tasks was not used to inform either the CAM diagnosis or the MDAS severity rating of delirium.

Given that the distributions of most of the cognitive test data were non-normal, and that variances were not always, homogeneous between groups, non-parametric statistics were used to compare all experimental data between groups. Kruskal-Wallis tests, known in the art, were first used to look for overall differences among the three groups. Mann-Whitney U tests, as known in the art, were then used to perform pairwise group comparisons. Receiver operating characteristic (ROC) analyses, as known in the art, were also conducted for the eight attention tasks to assesthe ability of each to discriminate delirium from dementia and cognitively normal patients. Statistical significance in all cases was taken as a two-sided p value<0.05.

The three groups were well-matched in terms of age and sex distribution, as shown in table 5. However, there were significant between-group differences in MDAS and MMSE scores. As expected, MDAS scores were higher in the delirium group than both the dementia (U=3.5, p<0.001) and the cognitively normal control group (U=37.0, p<0.001), showing a higher severity of delirium symptoms in this group in line with group classification. Patients with dementia also had higher MDAS scores than healthy controls (U=45.0, p<0.001). As expected, both the delirium (U=0.0, p<0.001) and the dementia (U=15.5, p<0.001) patients scored lower than cognitively healthy control patients on the MMSE, indicating higher levels of cognitive impairment in the two clinical patient groups. Patients with delirium also scored significantly lower than dementia patients on the MMSE (U=83.0, p<0.01), showing that levels of general cognitive impairment were highest in the delirium group.

TABLE 5

Demographic and Clinical Characteristics of the three Patient Groups.

| | Delirium (N = 20) | Dementia (N = 18) | Control (N = 20) | group comparisons |
|---|---|---|---|---|
| No. (%) male | 6 (30%) | 7 (39%) | 6 (30%) | chi square = 0.54, p = 0.8 |
| Age (yrs) Mean (SD) | 81.7 (8.8) | 82.1 (6.4) | 79.9 (8.0) | F = 0.44, p = 0.64 |
| MDAS: median score (range) | 12.5 (7-19) | 5.0 (2-9) | 2.0 (0-5) | K-W chi square = 23.39, p < 0.001 |
| MMSE: median score (range) | 16.0 (10-22) | 21.0 (12-25) | 27.0 (24-30) | K-W chi square = 39.92, p < 0.001 |

Not all patients completed all of the vigilance tasks, resulting in some missing data. Specifically, eight patients in the delirium group, two in the dementia group and two of the control patients were unable or unwilling to complete all of the tasks due to becoming too drowsy, agitated or uncomfortable. Two further patients in the delirium group did not have use of one or both hands at the time of testing, and so were unable to complete all of the button-pressing tasks. One further dementia patient was unable to complete the testing session due to time constraints, and one task was omitted for one of the control patients due to experimenter error. The final numbers of patients in each group therefore differed amongst tasks, as shown in table 6.

FIGS. 5(a) to 5(h) show boxplots of the group results in the 8 tasks. The median value and interquartile range of each dataset are represented by the position of the thick horizontal bar and the height of the inner box respectively. The positions of the upper and lower bars of each plot represent the maximum and minimum non-outlier values respectively. Outliers and extreme outliers are represented by open circles and stars respectively. Note that, due to the low range of values in the datasets, the maximum and minimum, inter-quartile range or median values are the same in some datasets, and so cannot be distinguished on the plots. Kruskal-Wallis tests showed that there were significant differences between the performances of the 3 groups for all 8 tasks (Task 1: H=30.53; Task 2: H=34.07; Task 3: H=30.98; Task 4: H=22.18; Task 5: H=17.56; Task 6: H=19.99; Task 7: H=19.01; Task 8: H=23.60; all at p<0.001).

As shown in FIGS. 5(a) to 5(h), patients in the delirium group scored lowest in all eight of the attention tasks. Their scores were significantly lower than both the cognitively normal control group (Task 1: U=36.0; Task 2: U=1.5; Task 3: U=17.0; Task 4: U=20.5; Task 5: U=30.0; Task 6: U=13.5; Task 7: U=18.0; Task 8: U=5.0; all at p<0.001) and the dementia group (Task 1: U=30.0, p<0.001; Task 2: U=18.0, p<0.001; Task 3: U=23.0, p<0.001; Task 4: U=50.5, p=0.003; Task 5: U=38.5, p=0.001; Task 6: U=22.5, p<0.001; Task 7: U=21.0, p<0.001; Task 8: U=9.5, p<0.001). Patients with dementia did not differ from controls on any task except task 4 (Task 1: U=159.5, p=0.55; Task 2: U=145.5, p=0.61; Task 3: U=148.5, p=0.50; Task 4: U=89.5, p=0.035; Task 5: U=143.5, p=0.57; Task 6: U=127.0, p=0.57; Task 7: U=125.0, p=0.53; Task 8: U=134.5, p=0.99). In task 4, in which patients had to count illuminations occurring at two locations with the presence of distracting stimuli, patients with dementia made fewer correct responses than the control group.

As patients with delirium had lower MMSE scores than the dementia patients, it is possible that their poorer performance on the vigilance tasks was due to their increased level of overall impairment rather than the presence of their delirium per se. In order to rule out this possibility, separate analyses were carried out on the data of 12 delirium patients who had the highest MMSE scores in their group, and 12 dementia patients with the lowest MMSE scores, who all completed the first two of the verbal-response tasks. The patients in these two subgroups did not differ in age (delirium mean (SD)=78.7 (8.6) years; dementia mean (SD)=81.1 (7.2) years; t (22)=0.75, p=0.46), and the delirium group still had the expected higher ratings of delirium severity on the MDAS (delirium median (range)=10.0 (7-17); dementia median (range)=5.5 (3-9); U=3.0, p<0.001). However, there was no difference between the MMSE scores of these two subgroups (delirium median (range)=19.5 (15-22); dementia median (range)=19.0 (12-21): U=69.0, p=0.89). Importantly, this subgroup of delirium patients still scored significantly lower than the subgroup of dementia patients on both of the verbal vigilance tasks compared (task 1: delirium median (range)=2.0 (0-5); dementia median (range)=4.5 (2-5); U=21.5, p<0.01: task 2 delirium median (range)=1 (0-3); dementia median (range)=4.5 (2-5); U=4.5, p<0.001).

The sensitivity of each task for detecting delirium was determined at each possible cut-off score. The specificity at each cut-off score was also determined separately for discriminating delirium from dementia and from cognitively-normal controls. Sensitivity and specificity values for the three highest cut-off scores for each task are shown in table 6. ROC curves were plotted to asses the overall accuracy of each task for discriminating delirium from each of the other patient groups. The area under the curve (AUC) of all plots fell between 0.802 and 0.995, indicating that all tasks had either good or excellent accuracy for discriminating delirium from dementia or cognitively normal patients, as shown in table 6.

Table 6 shows the sensitivity and specificity for delirium at selected cut-off scores for each task. Values are shown separately for detecting delirium and for discriminating it from Alzheimer's dementia and cognitively-normal patients. The area under the curve (AUC) values for the associated ROC curves are also shown for each task. In table 6, *=p<0.01 and **=p<0.001.

Patients with delirium performed poorly on a series of simple tasks involving sustained attention to visual information. They scored significantly worse than patients with Alzheimer's dementia, even when the two groups were matched on their level of overall cognitive impairment. All tasks showed either good or excellent accuracy for detecting delirium, demonstrating their utility as clinical diagnostic tools.

All eight of the tasks employed were highly accurate at discriminating patients with delirium from both cognitively normal patients and patients with Alzheimer's dementia. As the tasks have simple instructions and are easy to administer, they are also ideally suited to routine clinical practice. Using visual rather than auditory stimuli also means that the tasks are more practical for noisy clinical environments that could limit the reliability of tasks involving auditory attention. The tasks therefore show promising utility as diagnostic tools that are both sensitive and specific to delirium. All the tasks seem to show excellent discriminatory power.

These findings provide good evidence that inattention in delirium is characterised by deficits in sustaining attention to information presented in the visual domain. It will be appreciated that similar sustained attentional deficits may also occur in other modalities, such as touch.

Figure 6:
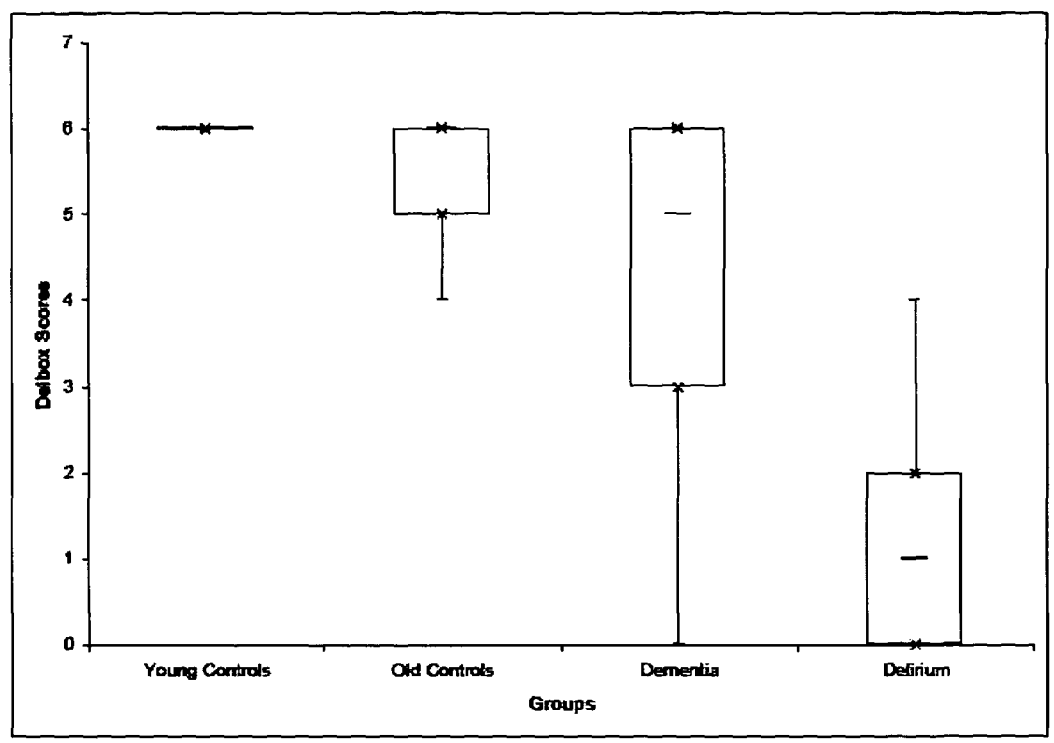
FIG. 6 is a box plot showing the results of further tests performed using the apparatus of FIG. 1.
Figure 7A:
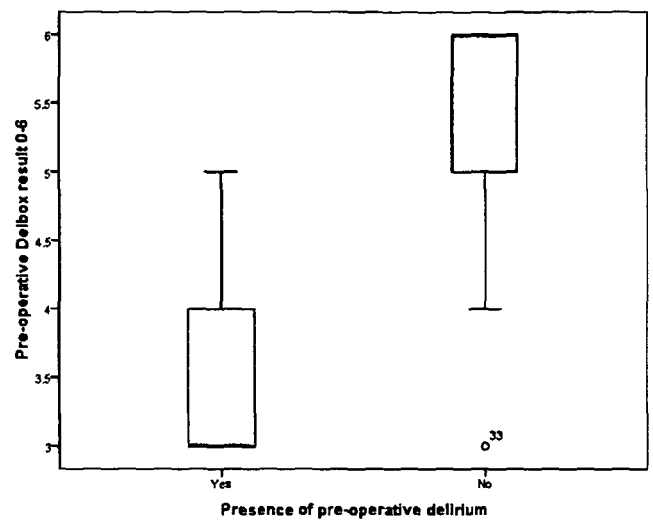
FIGS. 7a to 7e are box plots showing the results of further tests performed using the apparatus of FIG. 1 at different times before and after hip operations were performed on the subjects of the tests'
Figure 7B:
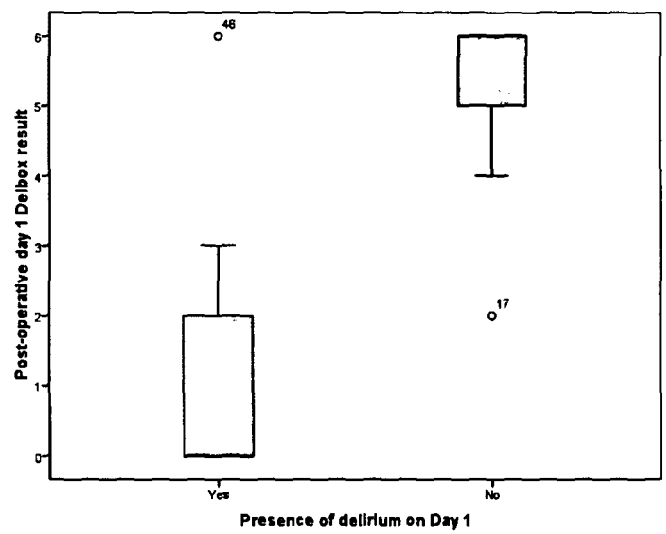
Figure 7C:
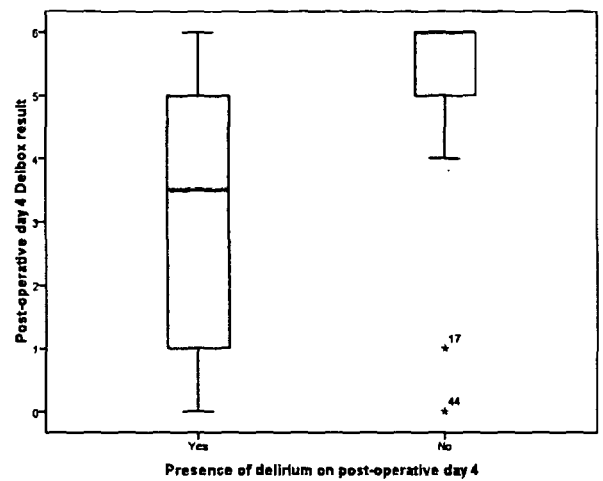
Figure 7D:
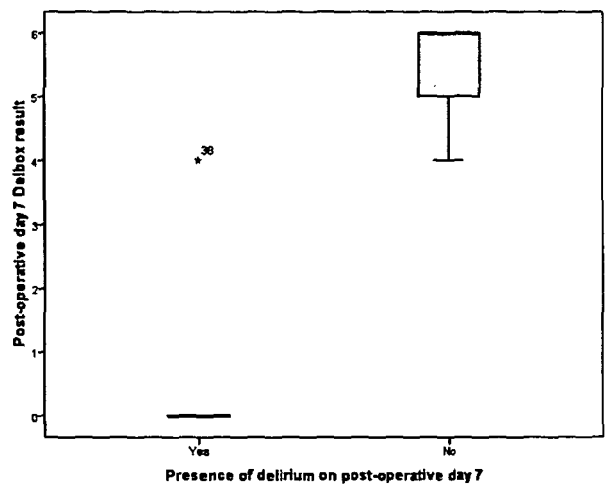
Figure 7E:
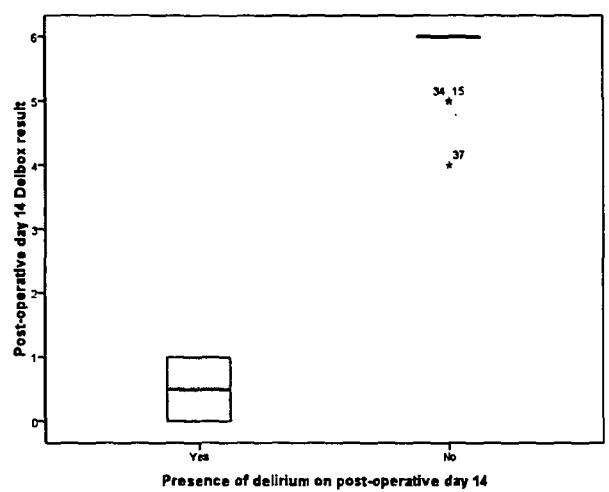

A further trial was performed on 20 subjects in each of the following groups:—(a) young, healthy controls, (b) older, cognitively normal controls, (c) patients with dementia, and (d) patients with delirium. The trial consisted of performance of a six block test with distractors (task 2). A boxplot of the results of the test is shown in FIG. 6, and it can be seen that performance of the delirium group was significantly worse than the dementia group and all the other groups, again showing that automated testing of patients using the device 5 can provide an effective test for the presence of dementia.

A further task using the device 5, was administered to a group comprising only young control subjects, none of whom was expected to show symptoms of delirium. The task was referred to as an extended vigilance task, and it involved counting lights displayed by the device 5 with increasing rests between illuminations for an extended period of time for three trials. Each trial lasted 2 minutes.

In the first trial, there were three second gaps between stimuli and no errors were made by any of the subjects. In the second trial, there were five second gaps between stimuli and five errors were made by the subjects. In the third trial, there were seven second gaps between subjects and two errors were made by the subjects.

The results of the three trials on young healthy subjects of the extended vigilance task gave no significant indication of the presence of delirium or other cause of inattention, as expected. However, when questioned about the difficulty of the task, all subjects indicated that the trials with the longest rest between stimuli (7 seconds) were quite difficult; most reported issues keeping focus on what number they were meant to be on, and that their minds would drift the longer the gap between stimuli got.

The outcome of the extended vigilance task suggests that longer task durations (for example, 2 minutes or greater), and/or inter-stimulus delays of 5 seconds or more may cause errors in people without delirium (healthy young, old, and/or dementia-sufferers).

Figure 8:
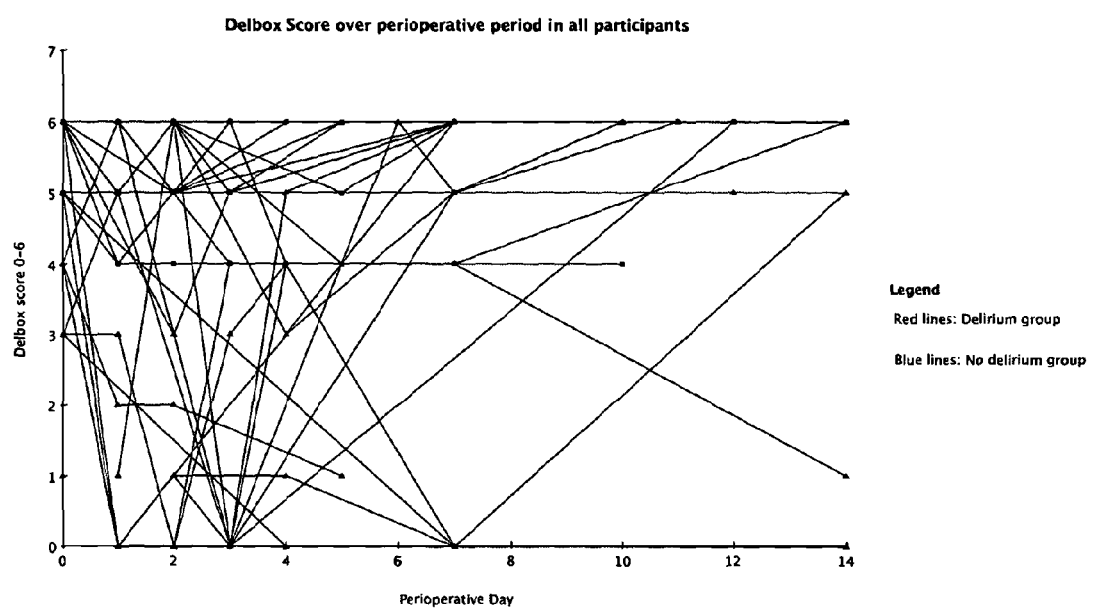
FIG. 8 is a plot showing the separation of scores achieved by delirium and non-delirium groups of subjects in the further tests illustrated in FIGS. 7a to 7e.

A further trial using the device 5 was performed on patients that had suffered hip fractures and were undergoing hip surgery. The results of the trial are illustrated in FIGS. 7 to 9.

The trial was performed on 61 subjects who were assessed for delirium pre-operatively, and at up to six further occasions over two weeks. The Confusion Assessment Method and Delirium Rating Scale-Revised 98 (DRS-R-98) was performed by the subjects to determine delirium presence and severity, and the Mini-Mental State Examination to assess global cognition.

The subjects also performed tasks using the device 5. The automated tasks using the device took up to 5 minutes to complete in comparison to the much longer periods required for the DRS-R-98 assessment. Group comparisons were made using Mann-Whitney U, and Spearman's Rho correlations between scores obtained from the automated tests using the device 5 and the outcomes of the DRS-R-98 assessments. Receiver Operating Characteristic (ROC) analyses were undertaken to assess the ability of the automated testing using the device 5 to discriminate delirium from controls.

The results of the pre- and post-operative trials are provided in Table 7.

TABLE 7

EDTB score in delirium vs no delirium at time of assessment

| Day | N Cases | N Controls | Median (IQR) Delirium | Median (IQR) No delirium | p | Area Under ROC Curve |
|---|---|---|---|---|---|---|
| 0 | 3 | 37 | 3 (3-4) | 6 (5.-6) | 0.005 | 0.892 |
| 1 | 9 | 32 | 0 (0-2.) | 6 (5.-6) | 0.000 | 0.981 |
| 2 | 7 | 30 | 1 (0.5-3.5) | 5.5 (5-6) | 0.003 | 0.979 |
| 3 | 5 | 12 | 0 (0-3.) | 6 (5-6) | 0.001 | 0.955 |
| 4 | 10 | 30 | 3.5 (1-5) | 6 (5-6) | 0.002 | 0.944 |
| 7 | 5 | 25 | 0 (0-0) | 6 (5-6) | 0.000 | |
| 14 | 2 | 17 | 0.5 (0-1) | 6 (6-6) | 0.006 | |

IQR = Inter-quartile range

The overall rate of delirium was 42.6%. Participants with active delirium scored significantly lower on the task using the device 5 than controls. EDTB scores correlated negatively and significantly with DRS-R-98 scores at every stage (p's<0.005).

Plotting scores obtained using the device 5 longitudinally over the perioperative period against DRS-R-98 scores revealed that the scores obtained using the device 5 deteriorated as delirium developed, and improved as delirium abated, as illustrated in FIGS. 7 to 9.

FIGS. 7a to 7e show boxplots of the results of the trial for subjects pre-operatively and at one day, four days, seven days and fourteen days after a hip operation. As before, the median value and interquartile range of each dataset are represented by the position of the thick horizontal bar and the height of the inner box respectively. The positions of the upper and lower bars of each plot represent the maximum and minimum outlier values respectively. Outliers and extreme outliers are represented by open circles and stars respectively.

FIG. 8 shows results of the tests using the device 5 for subjects exhibiting delirium and not exhibiting delirium (assessed using the DRS-R-98 assessment). This shows very good separation between the delirium and non-delirium groups in the results of the tests using the device 5. A ceiling effect is also present which suggests that by making the test slightly more difficult, even better distinction between the groups might be obtainable.

Figure 9A:
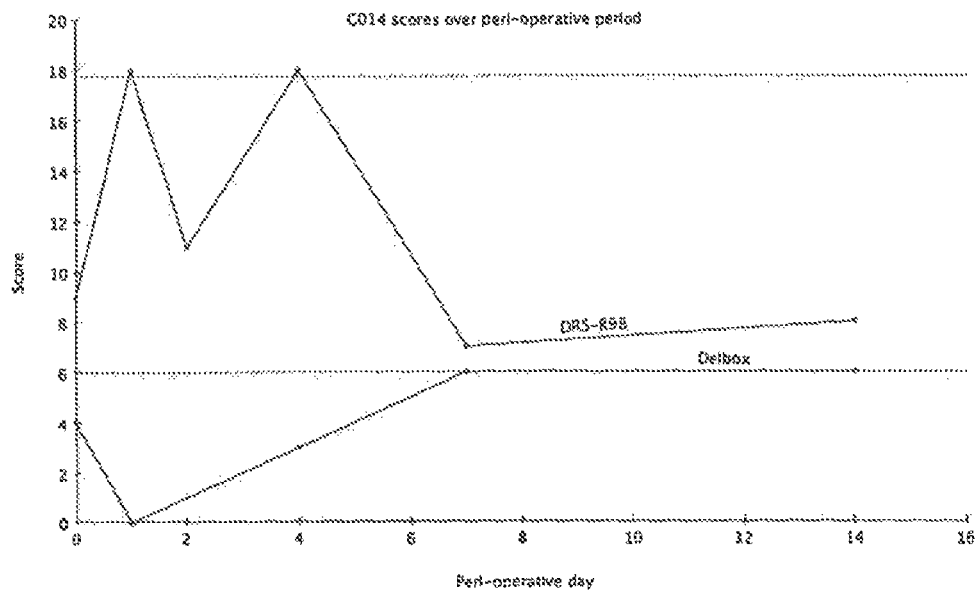
FIGS. 9a to 9c are plots showing test scores achieved by individual patients in the tests whose results are illustrated in FIGS. 7 and 8, compared to scores achieved by those patients in other delirium assessment procedures.
Figure 9B:
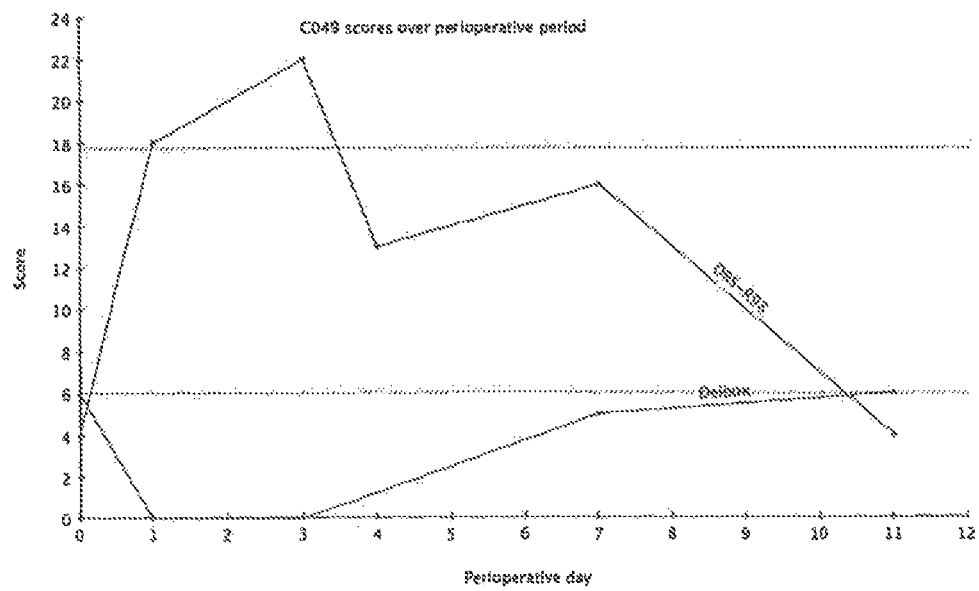
Figure 9C:
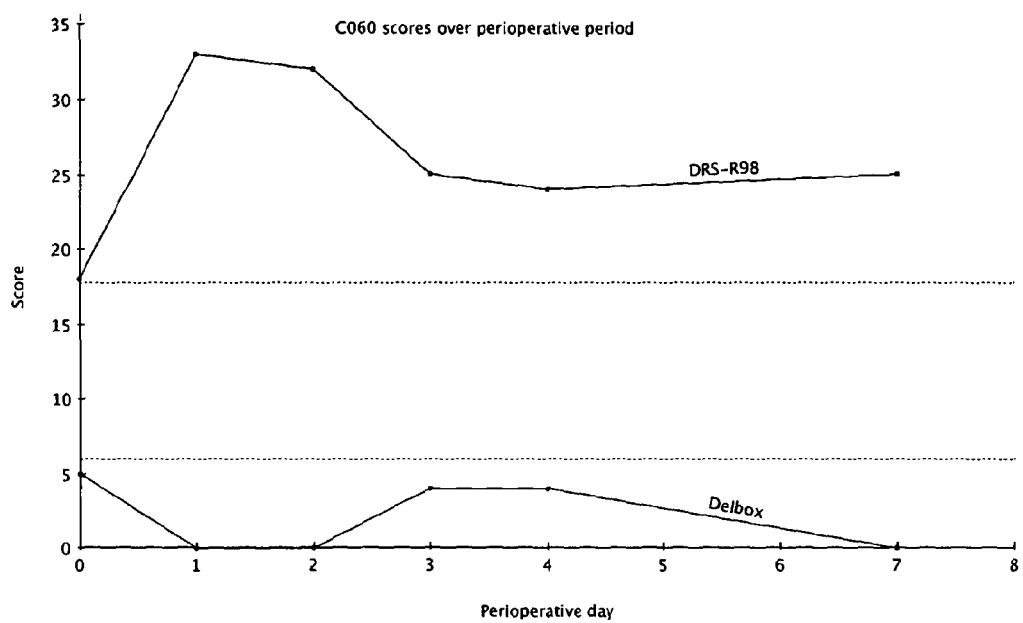

FIGS. 9a to 9c are plots of comparisons of scores obtained by individual patients the trial using the device 5 and according to further delirium assessments performed using the Delirium Rating Scale-Revised-98 assessmnet, which is the most established detailed delirium rating scale in use.

The top dotted lines in FIGS. 9a to 9c represents the published cut-off score (17.75) for delirium according to the DRS-R-98 assessment. Scores above that threshold are likely to represent delirium according to published data. However that assessment is not flawless and patients assessed by other means (for example, the Confusion Assessment Method) may score below 17.75 on the DRS-R-98 assessment.

The bottom dotted line in each of FIGS. 9a to 9c represents the maximum possible score (six out of six) for the tasks performed using the device 5. Current data suggests that scores of 5/6 or 6/6 are unusual in patients with delirium.

The data shown in FIGS. 9a to 9c suggest clearly that scores obtained on the automated tests using the device 5 parallel scores obtained using the DRS-R-98 assessment.

The trial performed on subjects pre- and post-operatively provides further evidence that the test of sustained visual attention with distractors using the device 5 performs well in detecting delirium, in this case in elderly patients around the time of acute hip fracture surgery. It also has the potential to be used longitudinally for objective monitoring of the severity of attentional deficits in delirium.

The tasks used in the studies described herein are designed to be as simple as possible, so as to ensure that any deficits observed most likely represent genuine deficits of sustained visual attention. Nevertheless, it is impossible to develop any task to be a completely 'pure' measure of any one neuropsychological function, and it is important to consider alternative explanations that could account for the patterns of behaviour that were found. As patients were impaired at these tasks regardless of whether verbal or motor responses were required, their poor performance cannot be accounted for by specific impairments related to either one of these response modes. Furthermore, as patients with delirium were impaired on these tasks compared to Alzheimer's patients matched in overall cognitive impairment, it is unlikely that their deficits represent more general difficulties related to understanding or remembering task instructions. However, it is possible that, rather than reflecting impairments in the neurocognitive systems underlying sustained attention, patients' impairments actually represent more fundamental deficits of arousal or consciousness that are associated with delirium, as described in Meagher, 2008 2030/id. Indeed, behavioural indicators of drowsiness were observed in some patients during test sessions. Further experiments are therefore now required to examine the extent to which patients' deficits in arousal and attention can be dissociated from one another. One limitation of the first study is that, whereas cognitively normal and delirium patients were recruited from hospital in-patient wards, patients in the dementia group were recruited from an outpatient memory clinic. This recruitment strategy was chosen due to the high prevalence of mixed dementia and delirium that occurs in inpatient settings, as described in Laurila, 2004 932/id. Recruiting dementia patients from an outpatient clinic, and also excluding patients in the delirium group with any known history of cognitive impairment, therefore helped to ensure that case ascertainment was as accurate as possible. Nevertheless, it is possible that patients with dementia might perform differently on these tasks when recruited from, and tested in, an inpatient ward environment. Further studies looking at the ability of inpatients with dementia, and also cases of mixed delirium and dementia, would therefore now be useful to determine how well these groups can be discriminated according to their performance on these tasks.

In sum, the tasks used in this study show much promise in their ability to detect delirium and to discriminate it from Alzheimer's dementia. The simple and portable nature of the tasks also makes them ideally suited to routine clinical practice. The results of this study support and extend previous suggestions that patients with delirium have specific impairments in sustained attention.

The provision of a simple device that can provide for automated or semi-automated tests based on sustained visual attention that can provide good performance in detecting the presence of delirium and distinguishing it from other possible conditions provides for increased efficiency in testing for the presence of delirium particularly in clinical settings. The tests can be administered by non-skilled or non-expert staff and can be performed in five minutes or less. Performance of the tests provides little disruption or distress to the subjects. In contrast known assessment procedures (for example using the DRS-R-98 assessment) must be performed by a trained clinical practitioner, and take significantly longer to perform. Such known assessments are at least partially subjective in nature, and can be more disruptive for the patient and, in some cases, it may be detrimental to the patient's welfare to perform the assessments.

The automated testing for delirium using the device 5 has the potential to become a standard clinical tool that can be performed at many stages in clinical practice, for example in initial assessments by GPs, in A&E, pre- and post-operatively, and in monitoring of individual, particularly aged, patients over extended periods of time.

It is important to note that the device 5 does not represent merely a device for automating previously known tests, and that the procedures performed using the device are not merely variants of previously known tests. It is a discovery pursuant to the present invention that by measuring a patient's sustained attention using automated or semi-automated, time-dependent cognitively simple tests on a portable device an accurate and objective test for the occurrence of delirium can be obtained.

It has been found to be important to provide a simple interface (for example, a plain surface with one or two lights) in order to successfully measure sustained attention without increasing the cognitive demands of the testing. The testing provided by the device 5, is based on accurate control and variation of the timing of visual or other physical stimuli to a subject, and the monitoring of responses, and the timing of responses, to such stimuli, in order to obtain accurate, repeatable results that can be correlated with, or used to determine the presence of, delirium.

The slow pace of the tests is also important, because this places greater demands on the capacity for sustained attention. The optimal speed of presentation of stimuli for counting up may be about one stimulus per second. By stretching this out to about one stimulus per 3 seconds and having several trials (i.e. 5 lights, 7 lights, etc.), the kind of attentional deficits that are particularly important in delirium may be elicited. Adding distracters appears to improve the performance of the tasks further.

The invention is not limited to the particular sequences of stimuli, distractions and timings described in relation to FIGS. 1 to 9. It will be appreciated that other sequences of stimuli and timings can also be used to determine the presence of delirium. For instance in further embodiments it has been found to be beneficial to ensure that inter-stimulus delays are between 800 ms and 4500 ms, or between 2050 ms and 4050 ms.

Usually any further sequences will be trialled on a group of reference subjects who are also subject to other, known assessments (for example, the DRS-R-98 assessment) so that the scores obtained using the sequence of stimuli can be correlated with the presence or absence of delirium.

Data representative of sequences of target stimuli and, for example, distraction stimuli can be stored on a disc, computer memory, or other storage device and can be downloaded to the device for performance of tests when desired.

A further embodiment of the device 50, and a system incorporating the device 50 is illustrated in FIGS. 10 to 13.

Figure 10:
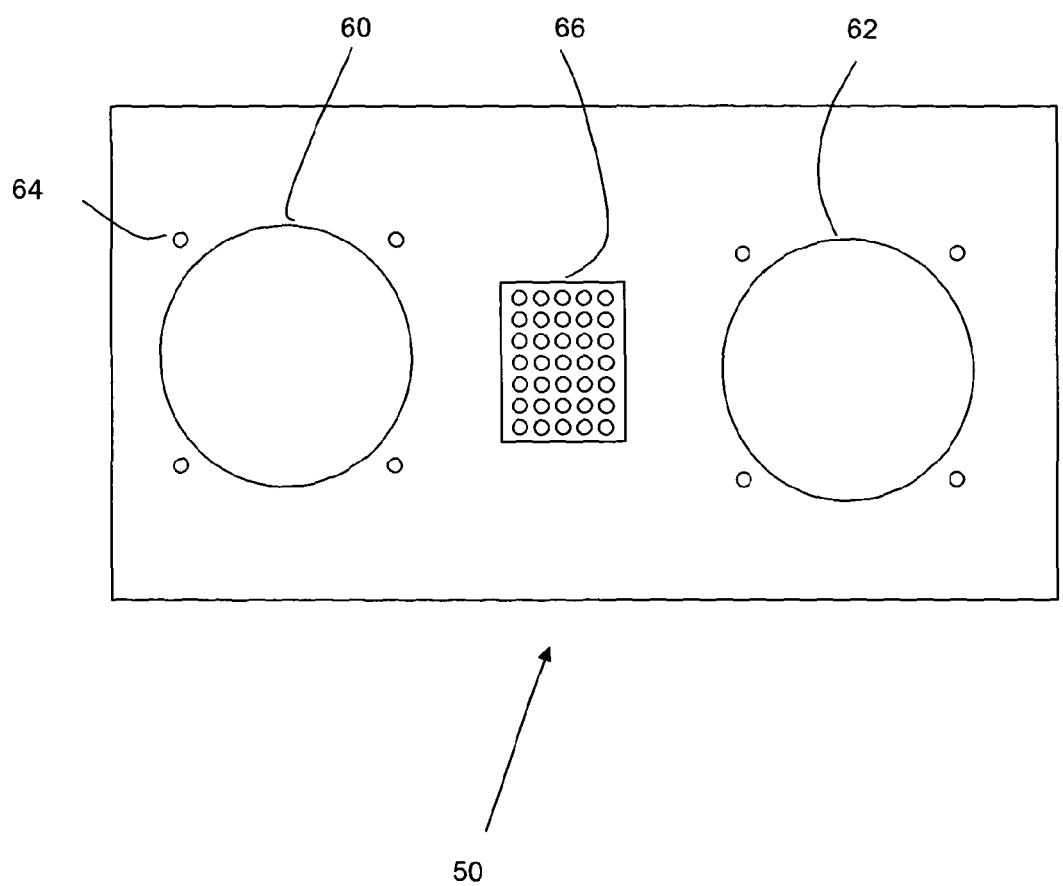
FIG. 10 is a schematic illustration of an apparatus for determining a measure of sustained attention according to a further embodiment.
Figure 11:
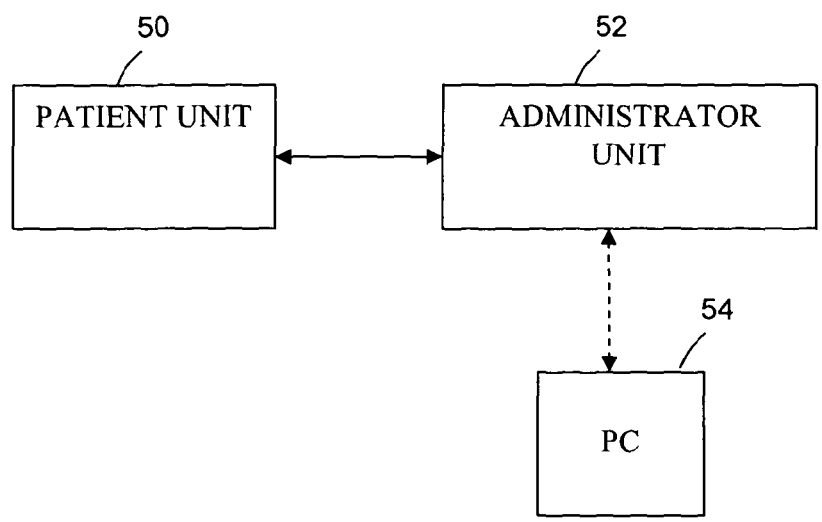
FIG. 11 is a schematic illustration of a system including the apparatus of FIG. 10.
Figure 12:
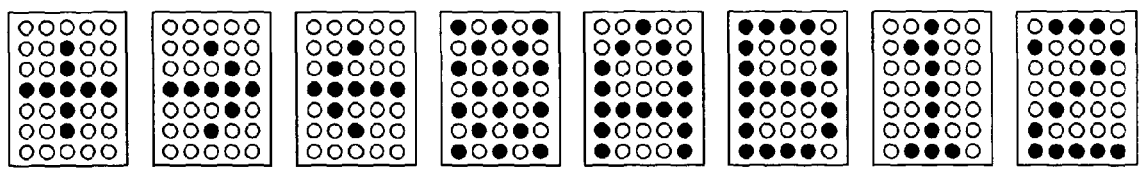
FIG. 12 is an illustration of outputs provided by an LED array of the apparatus of FIG. 10.

The front surface of the housing of the device 50 of the further embodiment is shown schematically in FIG. 10.

The device 50 does not include an operator interface. Instead the operator interface is provided on a separate administrator unit 52, which also includes a further processor for controlling operation of the device 50, as illustrated schematically in FIG. 11. The administrator unit includes further memory for storing multiple sets of test results. The administrator unit 52 is connected to the device 50 using a cable in the embodiment of FIG. 11, but can communicate with the device 50 using a wireless link in variants of the embodiment. In operation, the administrator unit 52 sends control signals to the device 50 to instruct the device 50 to display sequences of lights in accordance with a selected operating procedure or task, and receives data from the device 50 that is representative of the user's responses to the stimuli. The functionality of the administrator unit and the device 50 in combination is similar to that of the device 5. The device 5 and the device 50 include many of the same or similar components.

The device 50 of FIG. 10 includes a microprocessor, for example a Microchip Pic24F series microprocessor, a Maxim Max7219 LED driver and an ST Microelectronics ST232 series RS232 transceiver installed inside an ABS plastic housing produced by Teko.

The administrator unit 52 can be connected to a PC or other computer 54 via a wireless or wired link, for instance a USB link, which allows for patient test results to be uploaded to the PC for storage and further analysis. The link to the PC or other computer 54 also allows new test progams, for example new tasks, to be downloaded to the administrator unit or the device 50.

The administrator unit includes a Microchip Pic24F series microprocessor, a Microchip 24LC256 series EEPROM memory and an ST Microelectronics ST232 series transceiver. The administrator unit includes a flash drive for storing program data. The program data is modifiable by writing a text file on a PC then downloading the text file to the flash drive. The administrator unit also comprises an Evatron ABS plastic housing, within which the other components are installed.

As shown in FIG. 10, the front face of the device 50 comprises two illuminable push switches 60, 62 (in this case Starpoint CPB series devices) that the user is instructed to press in response to their being illuminated during a test.

A number of small LEDs (in this case Hewlett Packard HPLMP-EG10 series LEDs) are mounted underneath the top panel of the device 50 and are visible only when illuminated. Thus, the pushbuttons 60, 62 are the only items on the front face of the device 50 that are visible to the user when the LEDs are not illuminated.

The LEDs consist of four small LEDs 64 placed around each of the large pushbutton switches ('peripheral leds') and a central array 66 of LEDs. The central array 66 of LEDs is arranged in a 5 by 7 matrix in the embodiment of FIG. 10. Such an array is capable of displaying a wide range of different characters including symbols, numbers and letters. Some examples are illustrated schematically in FIG. 12. In a variant of the embodiment the central array 66 comprises a 7 by 7 matrix.

Figure 13:
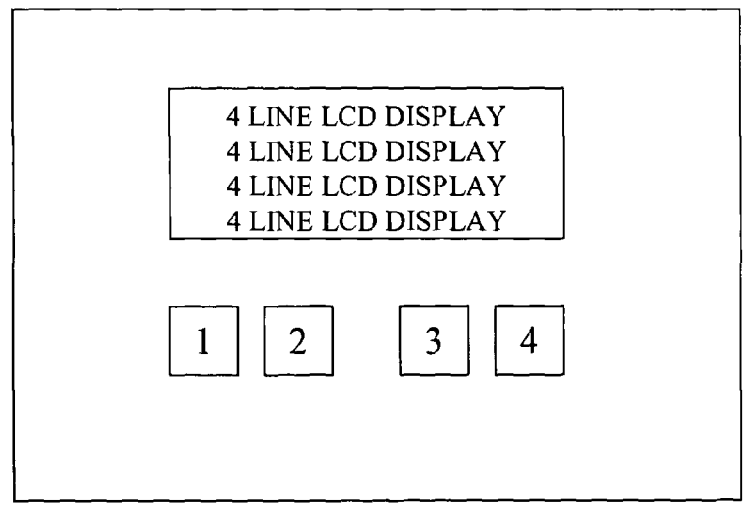
FIG. 13 is a schematic illustration of an administrator unit forming part of the system of FIG. 11.

The top face of the administrator unit 52 is illustrated schematically in FIG. 13, and comprises a 4-line alphanumeric LCD display (in this case a Powertip Corporation display) and four push-button switches. The push button switches have different functions depending on context and whose functions are indicated on the LCD. In a variant of the embodiment of FIG. 13 the administrator unit has an alphanumeric keypad for control and data entry rather than the four push-button switches shown in FIG. 13.

The system of FIGS. 10 to 13 is designed to be simple to use, both by the operator (also referred to as a test administrator) and by the test subject (also referred to as a patient or user). The LCD on the administrator unit 52 displays text prompts that guide non-specialist operators through the testing process, for example prompting them to select task sequences and to provide instructions to the subject. Each task generally lasts no more than 1 minute or so but a patient may do more than one task in succession.

As has already been described, tasks comprise sequences of target stimuli that are presented to the subject for short periods of time (for example, up to a few seconds). Stimuli are fully programmable but usually comprise one of the large illuminated switches lighting up or a certain character appearing on the central LED array. As well as the target stimulus, additional distracting stimuli (for example flashing peripheral LEDs) may also be presented in order to ascertain the subject's ability to maintain attention in the presence of distraction. Depending on the test the patient may be asked to respond to particular stimuli by counting the number of times they occur or by pressing one or other of the buttons.

In verbal response tests the subject is asked by the test administrator to count the occurrence of specific stimuli (typically, but not necessarily, the large lights inside the switches) on the device 50 while ignoring any other stimuli that might appear. The subject makes no direct responses to any of the stimuli. When the test is complete the subject reports verbally to the test administrator what they have observed. The test administrator then enters this information on the administrator unit 50. During the testing the administrator unit presents text prompts to the test administrator to guide them through the test process.

The following is an example of a text prompt provided by the administrator unit 52 to a test administrator:—
Instruction:
Count flashes of A
4: Start
The next text prompt would then be:—
Test in progress:
Step 1 out of 5
And when the test was completed, the text prompt would be:—
Test complete:
Enter patient count
Count: 4
1:↑2:↓4:ENTER
Where the numerals 1, 2 and 4 in the last line refer to the numbered push buttons on the administrator unit.

In button response tests the subject is asked to respond to the occurrence of certain stimuli by pressing one or other of the two switches 60, 62 on the device 50. In these tests no verbal response is required from the patient and all measurements are performed automatically by the administrator unit 52 as the test proceeds. Again the administrator unit can provide prompts to the test administrator as the tests proceed.

The system of FIGS. 10 to 13 is fully programmable to allow the development and trialling of various different types of stimuli and sequences of stimuli. All the available stimuli can be used in a flexible manner. Test patterns can be developed separately and then downloaded to the system. The test administrator can select from all currently available tests, if desired.

Test results, either verbal responses entered by the administrator or time-dependent measurements obtained automatically can be stored in non-volatile memory of the administrator unit 52 and may be uploaded to a PC 54 or other computer for further analysis. In practice it is likely that a patient will undertake a range of tests and that the results of the tests will be grouped together for ease of later analysis.

Although an example of use of the apparatus to measure attention deficits and then use this to determine a measure of delirium is described, it will be appreciated that the device and at least some of the associated methodology is also usable in investigating/determining measures of other behaviours and/or conditions, such as Attention Deficit and Hyperactivity Disorder, Traumatic Brain Injury or Drug/Alcohol intoxication or other research. Furthermore, whilst certain tasks, operations, stimuli, distractions and timings have been described, it will be appreciated that the device may be adapted or programmed for use with other tasks, which may comprise different stimuli, distractions, timings, delays, cues or other factors.

A skilled person will also appreciate that variations of the disclosed arrangements are possible without departing from the invention.

For example, although the invention is described in terms of a portable, stand-alone device, a skilled person would appreciate that it may be possible to implement the device using a suitably programmed and adapted computer system.

For instance, in certain embodiments the device may comprise a tablet computer, for example an iPad, a smart phone, other portable computing device. In such embodiments the stimulus providers may for example be in the form of areas of the display of the tablet computer or smart phone that are lit, coloured or otherwise highlighted in a desired sequence under control of software installed on the tablet computer or smart phone. The software may be in the form of one or more apps.

The tablet computer, smart phone or other portable computing device may include any suitable operating system, for example Android or Apple iOS, and the software may be installed and operated under such operating system. The software may be provided and operated independently of other software on the device. Alternatively the software may be included in a suite or package of medical or other applications.

In embodiments in which the device comprise a tablet computer, for example an iPad, a smart phone, or other portable computing device, a touchscreen user or operator interface may be provided for data logging or control of the operating procedures. Collected data may be gathered and analysed at the device. Alternatively or additionally, the data may be transmitted over a network or internet connection for remote storage and analysis. The data may be stored or analysed in combination with other user data, for example other medical record data associated with the user.

Embodiments implemented in the form of a tablet computer, smart phone or other touchscreen device may be particulary suitable when it is desired that the device comprises a substantially plain surface to reduce extraneous user distraction, as many such devices comprise touchscreens without keyboards, with plain housing and with few or no other user input devices other than the touchscreen provided on the surface.

Although the stimulus provider has been described as comprising lights in certain embodiments, in alternative embodiments any suitable form of stimulus provider may be provided and the target stimuli may, for example, comprise any suitable visual and/or tactile and/or audible stimuli. For example, the stimuli may comprise parts of a display, for example a computer or phone display, that are selectively lit, coloured or otherwise highlighted. Alternatively, the stimuli may comprise text for example individual letters.

Furthermore, although the device is described as having in-built displays 25 and input devices 15, 20, it will be appreciated that other, external displays and/or input devices may be provided.

Additionally, although the device is described as having an LED display and LED lit buttons, it will be appreciated that other display/lighting types may be used, such as LCD displays, incandescent bulbs, OLEDs, cathode ray displays and the like.

Although the described embodiments are suitable for testing a user's sustained attention, variants of the embodiments may be used for testing other forms of attention, for example focused attention or attention shifting.

The above description of specific embodiments is by way of example only and not for the purposes of limitation. It will be clear to the skilled person that minor modifications may be made without significant changes to the operation described.

Each feature disclosed in the description, and (where appropriate) the claims and drawings may be provided independently or in any appropriate combination.

TABLE 6

| Task | Cut off score | Sensitivity to Delirium | | Delirium vs. Dementia | | | Delirium vs. Cognitively-Normal Controls | | |
|---|---|---|---|---|---|---|---|---|---|
| | | | | Specificity | | | Specificity | | |
| | | Cases/total | % | Cases/total | % | AUC | Cases/total | % | AUC |
| 1 | 5 | 19/20 | 95.0 | 12/18 | 66.7 | 0.917** | 16/20 | 80.0 | 0.910** |
| | 4 | 17/20 | 85.0 | 16/18 | 88.9 | | 18/20 | 90.0 | |
| | 3 | 11/20 | 55.0 | 17/18 | 94.4 | | 18/20 | 90.0 | |
| 2 | 5 | 18/18 | 100 | 10/18 | 55.6 | 0.944** | 11/18 | 61.1 | 0.995** |
| | 4 | 18/18 | 100 | 15/18 | 83.3 | | 17/18 | 94.4 | |
| | 3 | 15/18 | 83.3 | 16/18 | 88.9 | | 18/18 | 100 | |
| 3 | 5 | 16/17 | 94.1 | 12/18 | 66.7 | 0.925** | 15/19 | 78.9 | 0.947** |
| | 4 | 14/17 | 82.4 | 16/18 | 88.9 | | 18/19 | 94.7 | |
| | 3 | 13/17 | 76.5 | 17/18 | 94.4 | | 19/19 | 100 | |
| 4 | 5 | 14/15 | 93.3 | 7/17 | 41.2 | 0.802* | 15/18 | 83.3 | 0.924** |
| | 4 | 12/15 | 80.0 | 12/17 | 70.6 | | 16/18 | 88.9 | |
| | 3 | 10/15 | 66.7 | 14/17 | 82.4 | | 17/18 | 94.4 | |
| 5 | 5 | 12/14 | 85.7 | 7/17 | 41.2 | 0.838* | 8/19 | 42.1 | 0.887** |
| | 4 | 12/14 | 85.7 | 14/17 | 82.4 | | 19/19 | 100 | |
| | 3 | 11/14 | 78.6 | 16/17 | 94.1 | | 19/19 | 100 | |

TABLE 6-continued

| Task | Cut off score | Sensitivity to Delirium | | Delirium vs. Dementia | | | Delirium vs. Cognitively-Normal Controls | | |
|---|---|---|---|---|---|---|---|---|---|
| | | | | Specificity | | | Specificity | | |
| | | Cases/total | % | Cases/total | % | AUC | Cases/total | % | AUC |
| 6 | 5 | 12/12 | 100 | 9/16 | 56.3 | 0.883* | 11/18 | 61.1 | 0.938** |
| | 4 | 9/12 | 75.0 | 12/16 | 75 | | 16/18 | 88.9 | |
| | 3 | 9/12 | 75.0 | 13/16 | 81.3 | | 18/18 | 100 | |
| 7 | 5 | 10/11 | 90.9 | 10/16 | 62.5 | 0.881* | 14/18 | 77.8 | 0.909** |
| | 4 | 9/11 | 81.8 | 15/16 | 93.8 | | 16/18 | 88.9 | |
| | 3 | 8/11 | 72.7 | 15/16 | 93.8 | | 17/18 | 94.4 | |
| 8 | 5 | 11/11 | 100 | 10/15 | 66.7 | 0.942** | 12/18 | 66.7 | 0.975** |
| | 4 | 11/11 | 100 | 13/15 | 86.7 | | 15/18 | 83.3 | |
| | 3 | 9/11 | 81.8 | 14/15 | 93.3 | | 17/18 | 94.4 | |

The invention claimed is:

1. A testing apparatus for testing a user's attention to distinguish delirium from dementia and normal cognition, comprising a stimulus provider and a controller for controlling the stimulus provider to provide at least one target stimulus, wherein the controller is configured to perform at least one operating procedure and the at least one operating procedure comprises controlling the stimulus provider to provide a sequence of target stimuli to the user, wherein
the controller is configured to control the stimulus provider to provide a delay between each target stimulus of the operating procedure and the delay between each target stimulus is between 2050 ms and 4050 ms;
each stimulus is provided for a duration in the range between 600 ms to 1400 ms;
the sequence consists of between 1 and 14 of the target stimuli;
a combination of the delay, the duration and number of target stimuli in the sequence is selected to distinguish delirium from dementia and normal cognition; and
the operating procedure comprises a counting test and the apparatus comprises an input device configured to receive a user count of the number of the target stimuli in the sequence in a form of a single response, the input device comprising at least one of: a data input device for an operator to enter the response, or a user input device for the user to enter the response.

2. The apparatus according to claim 1, wherein the delay between stimuli is at least one of variable or random.

3. The apparatus according to claim 1, wherein the at least one operating procedure lasts for a duration of between 7 seconds and 180 seconds.

4. The apparatus according to claim 1, further comprising at least one distracter for providing distraction stimuli during the at least one operating procedure.

5. The apparatus according to claim 1 that comprises a housing for housing the apparatus, wherein the housing has a substantially plain surface, the stimulus provider is provided on the substantially plain surface, and the substantially plain surface excludes any user input devices or the stimulus provider other than those used for testing attention or receiving a user assessment.

6. The apparatus according to claim 5, wherein the stimulus provider comprises at least one light provided on the surface of the housing.

7. The apparatus according to claim 1 further comprising means for directing a user's attention to a predetermined location, wherein the predetermined location is a fixation point.

8. The apparatus according to claim 1 further comprising cueing device for alerting a user that a stimulus will be provided, before the stimulus is actually provided.

9. The apparatus according to claim 1, wherein the controller is configured to perform a test comprising a plurality of operating procedures, and each operating procedure in the test is different to at least one other operating procedure in the test.

10. The apparatus according to claim 9, wherein each operating procedure in the test has a different expected level of difficulty for the user to at least one other operating procedure in the test.

11. A system for determining a measure of a user's sustained attention comprising the apparatus according to claim 1, in which the controller is configured to perform a plurality of operating procedures to obtain a plurality of the responses, and a processor for processing the responses to determine a measure of the user's sustained attention, wherein the processor is configured to compare the measure of the user's sustained attention determined to a threshold and to provide an output signal in dependence on the comparison, wherein the output signal is representative of an indication that the user may suffer from delirium.

12. The apparatus according to claim 1, wherein the apparatus comprises at least one of: a tablet computer, smart phone or other portable computing device.

13. A method of testing a user's sustained attention, comprising performing at least one operating procedure that comprises providing a sequence of between 1 and 14 target stimuli to the user and monitoring the user's response to the target stimuli, wherein the method further comprises:
providing a delay between each target stimulus of the operating procedure and the delay between each target stimulus is between 2050 ms and 4050 ms;
providing each stimulus for a duration in the range between 600 ms to 1400 ms;
selecting a combination of the delay, the duration and number of target stimuli to distinguish delirium from dementia and normal cognition;
performing a counting test comprising receiving a user count of the number of target stimuli in the sequence in a form of a single response; and
determining the presence of delirium based on a result of the counting test.

14. A testing apparatus for testing a user's attention, comprising at least one stimulus providing means and a controller for controlling the stimulus providing means to provide at least one target stimulus, wherein the controller is configured to perform at least one operating procedure and the at least one operating procedure comprises controlling the stimulus providing means to provide a sequence of target stimuli to the user, wherein the controller is configured to control the stimulus providing means to provide a delay between each target stimulus of the operating procedure and the delay between each target stimulus is between 2050 ms and 4050 ms;

each stimulus is provided for a duration in the range between 600 ms to 1400 ms;

the sequence consists of between 1 and 14 of the target stimuli;

a combination of the delay, the duration and number of target stimuli in the sequence is selected to distinguish delirium from dementia and normal cognition; and the operating procedure comprises a counting test and the apparatus comprises an input means configured to receive a user count of the number of the target stimuli in the sequence in a form of a single response, the input means comprising at least one of: a data input means for an operator to enter the response, or a user input means for the user to enter the response.

* * * * *